US008656779B2

(12) United States Patent
Adams et al.

(10) Patent No.: US 8,656,779 B2
(45) Date of Patent: Feb. 25, 2014

(54) DAMAGE DETECTION USING LASER VIBROMETRY

(75) Inventors: Douglas E. Adams, West Lafayette, IN (US); David Joseph Koester, Lafayette, IN (US); Sara Underwood, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 232 days.

(21) Appl. No.: 13/254,779

(22) PCT Filed: Mar. 5, 2010

(86) PCT No.: PCT/US2010/026368
§ 371 (c)(1),
(2), (4) Date: Sep. 2, 2011

(87) PCT Pub. No.: WO2010/102208
PCT Pub. Date: Sep. 10, 2010

(65) Prior Publication Data
US 2011/0314915 A1    Dec. 29, 2011

Related U.S. Application Data

(60) Provisional application No. 61/157,740, filed on Mar. 5, 2009, provisional application No. 61/158,215, filed on Mar. 6, 2009.

(51) Int. Cl.
*G01N 29/04*    (2006.01)

(52) U.S. Cl.
USPC .................. 73/582; 73/579; 73/597; 73/602

(58) Field of Classification Search
USPC ............................ 73/582, 579, 597, 599, 602
See application file for complete search history.

(56) References Cited

U.S. PATENT DOCUMENTS

| | | | |
|---|---|---|---|
| 3,020,751 A * | 2/1962 | Wohl | 73/668 |
| 4,752,140 A | 6/1988 | Cielo et al. | |
| 4,768,381 A * | 9/1988 | Sugimoto | 73/657 |
| 6,172,752 B1 * | 1/2001 | Haruna et al. | 356/503 |
| 6,505,130 B1 * | 1/2003 | Springer et al. | 702/40 |
| 6,915,217 B2 * | 7/2005 | Springer et al. | 702/40 |
| 7,812,963 B2 * | 10/2010 | De Groot | 356/497 |
| 8,154,731 B2 * | 4/2012 | Arnvidarson et al. | 356/451 |
| 8,462,350 B2 * | 6/2013 | Pfaff | 356/503 |
| 2003/0010128 A1 | 1/2003 | Buell et al. | |
| 2005/0023434 A1 | 2/2005 | Yacoubian | |
| 2006/0260407 A1 | 11/2006 | Donskoy et al. | |
| 2006/0262319 A1 | 11/2006 | Gatt | |

OTHER PUBLICATIONS

Extended European Search Report issued in European Patent Application No. 10749391.8 Sep. 11, 2013.
International Search Report and Written Opinion issued in PCT/US2010/026368. May 12, 2010.

(Continued)

*Primary Examiner* — J M Saint Surin
(74) *Attorney, Agent, or Firm* — John V. Daniluck; Douglas G. Gallagher; Bingham Greenebaum Doll LLP

(57) ABSTRACT

Methods and apparatus for exciting a structure and determining its structural integrity. In particular, methods of nonlinear analysis are used to compare first and second response datasets, each dataset resulting from a different excitation amplitude that the other dataset.

35 Claims, 22 Drawing Sheets

(a) Polytec 3D scanning laser vibrometer (b) Fiberglass composite panel (c) Piezoelectric actuator attached at skewed angle to excite three directions simultaneously
Aluminum base
Impedance head
Piezoelectric actuator
50 g mass

(56) References Cited

OTHER PUBLICATIONS

Response to Written Opinion filed in PCT/US2010/026368. Jan. 5, 2011.
International Preliminary Report on Patentability issued in PCT/US2010/026368. Oct. 18, 2011.
Underwood, Sara, et al., "Damage detection in sandwich composite materials using laser vibrometry in conjunction with nonlinear system identification," Proc. of SPIE, vol. 7295, pp. 1-11. Mar. 26, 2009.
Dantec Dynamics, "Automatic Shearography Inspection System for Helicopter Rotor Blades," Dantec Dynamics [on-line] available at http://www.dantecdynamics.com/Default.aspx?ID=1606. [Accessed Jun. 28, 2013]. Jun. 28, 2013.
Sundaresan, M., et al., "Experimental Damage Detection on a Wing Panel Using Vibration Deflection Shapes," Structural Health Monitoring, vol. 2, No. 3, pp. 243-256. Sep. 2003.
Ghosal, A., et al., "Experimental Investigation of Damage Detection in Composite Material Structures using a Laser Vibrometer and Piezoelectric Actuators," Journal of Intelligent Material Systems and Structures, vol. 14, No. 8, pp. 521-537. Aug. 2003.
Staszewski, W.J., et al., Smart Materials and Structures, vol. 13, No. 2, pp. 251-260. Feb. 4, 2004.
Storer, D.M., et al., "An Explanation of the Cause of the Distortion in the Transfer Function of a Duffing Oscillator Subject to the Sine Excitation," Proceedings of the International Modal Analysis Conference, vol. 2, pp. 1197-1205. 1991.
Johnson, T., et al., "Transmissibility as a Differential Indicator of Structural Damage," American Society of Mechanical Engineering Journal of Vibration and Acoustics, vol. 124, No. 4, pp. 634-641. Oct. 2002.

* cited by examiner

- Damage introduced to panel at known locations and sizes.

FIG. 2(a) Core cracking

FIG. 2(b) Disbond

DAMAGE DETECTION USING LASER VIBROMETRY

CROSS REFERENCE TO RELATED APPLICATION

This application is a national stage application of PCT/US10/26368, filed Mar. 5, 2010, and claims the benefit of priority to U.S. Provisional Patent Application Ser. No. 61/157,740, filed Mar. 5, 2009; and U.S. Provisional Patent Application No. 61/158,215, filed Mar. 6, 2009, both entitled DAMAGE DETECTION IN COMPOSITES USING LASER VIBROMETRY, all of which are incorporated herein by reference in their entirety.

GOVERNMENT FUNDING

This invention was made with government support under Grant Number N00164-10-R-JQ12 awarded by the U.S. Navy/ONR. The Government has certain rights in the invention.

FIELD OF THE INVENTION

This document pertains to methods for detecting damage in structures, and in particular to detection of damage and composite structures using velocity measurements.

BACKGROUND

Stiffened laminate and sandwich composite materials used in military aircraft includes multiple layers that exhibit subsurface damage mechanisms such as disbonds, ply cracking, core crushing, and core cracking, which usually cannot be identified using visual inspections. It is also difficult to inspect composite structures such as blades and fuselage sections using localized methods (e.g., coin tap, ultrasonic, thermographic, impedance) unless these structural components are first removed from the aircraft. Furthermore, these localized methods can detect damage within approximately $1/8$ inch of the surface, but do not penetrate into deep composite laminate or sandwich sections.

Laser shearography systems are commercially available for inspecting helicopter rotor blades, but these systems require that a vacuum be achieved prior to testing and that the blades be removed from the rotor for inspection. A number of researchers have applied single-dimensional laser vibrometry for detecting damage in metallic and composite materials based on the analysis of modal frequency responses, vibration curvatures, and strain energies in addition to propagating elastic waves. This prior work has focused on thin laminate composite sections with relatively simple geometries and damage mechanisms located close to the surface of the material. This work in damage detection using laser vibrometry has also relied on reference signatures that are acquired in undamaged specimens. As mentioned above, there is a need for inspection methods other than transmitted x-ray for detecting damage in deep composite sections. There is also a need for damage detection algorithms that do not involve a comparison with reference signatures because there are various composite structures throughout the aircraft that are geometrically complex and exhibit subtle changes in boundary conditions throughout the life of the aircraft.

Some embodiments of the present invention pertain to a vibration-based damage detection technique for composite materials by considering nonlinear changes in the forced frequency response of a fiberglass composite panel due to material damage. By utilizing vibration measurements, the technique addresses the need for wide area damage detection in large composite structures. There is also the potential to implement this inspection method without first removing the structures from the aircraft because a scanning laser vibrometer with a relatively long measurement range is used to acquire the vibration data. One embodiment of the present invention pertains to a reference free, non-linear method for detecting damage using vibration data.

SUMMARY OF THE INVENTION

Some embodiments of the present invention pertain to methods for exciting a composite panel, measuring its responses, and analyzing the responses with non-linear analysis techniques.

One aspect of the present invention pertains to a method for determining the structural integrity of a component. Other embodiments include vibrating the component over a range of frequencies at a first amplitude, and acquiring spatial response data of at least one point on the surface of the component. Still further embodiments include vibrating the component at a second amplitude different than the first amplitude, and acquiring velocity data for the point. Still further embodiments include correcting the first data based on the amplitude, correcting the second data based on the second amplitude, and identifying non-linear behavior of the point from.

Another aspect of the present invention pertains to a method for determining the structural integrity of a laminated structure. Some embodiments include establishing a multi-axis coordinate system on the structure, including a plurality of discrete points on the structure. Yet other embodiments include vibrating the structure in each axis of the coordinate system at a first amplitude, and measuring the multi-dimensional velocity at each of the points. Other embodiments include vibrating the structure in at least one axis at a second amplitude different than the first amplitude, and measuring the velocity data at each of the points. Some embodiments include comparing the measured velocity during vibrating at the first amplitude to the measured velocity during vibrating at the second amplitude; and determining the structural integrity of the structure.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is excessive and unnecessary.

BRIEF DESCRIPTION OF THE DRAWINGS

FIG. 2 are photographic images of (a) core damage and (b) disbond damage mechanisms.

Figure 11:
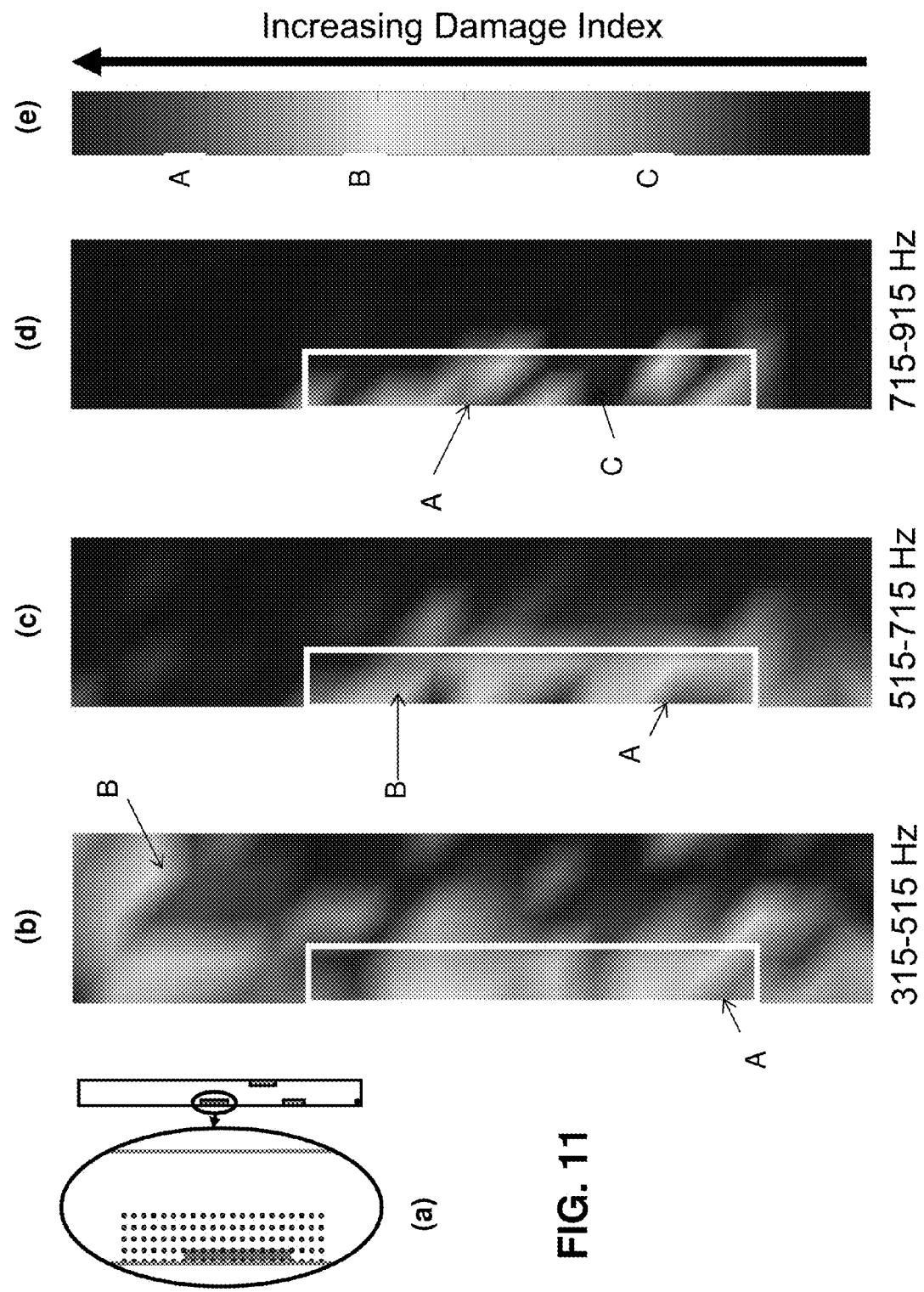

Some of the Figures including FIG. 11 include keys for interpreting the relative magnitudes of the damage indices plots. All shaded plots shown herein use "A" to indicate a high damage index, "B" to indicate a moderate damage index, and "C" to indicate a low damage "C."

FIG. 11 depict schematic and pictorial representations of the response of the panel in the vicinity of the cracked core, with (a) being a schematic representation of the location of the damage; (b) being a shaded representation of the field of damage indices in the vicinity of the core damage in a first frequency band, (c) in a second frequency band, (d) in a third frequency band, and (e) a graphical representation of the colors and shading used for the pictorially represented damage index.

Figure 12:
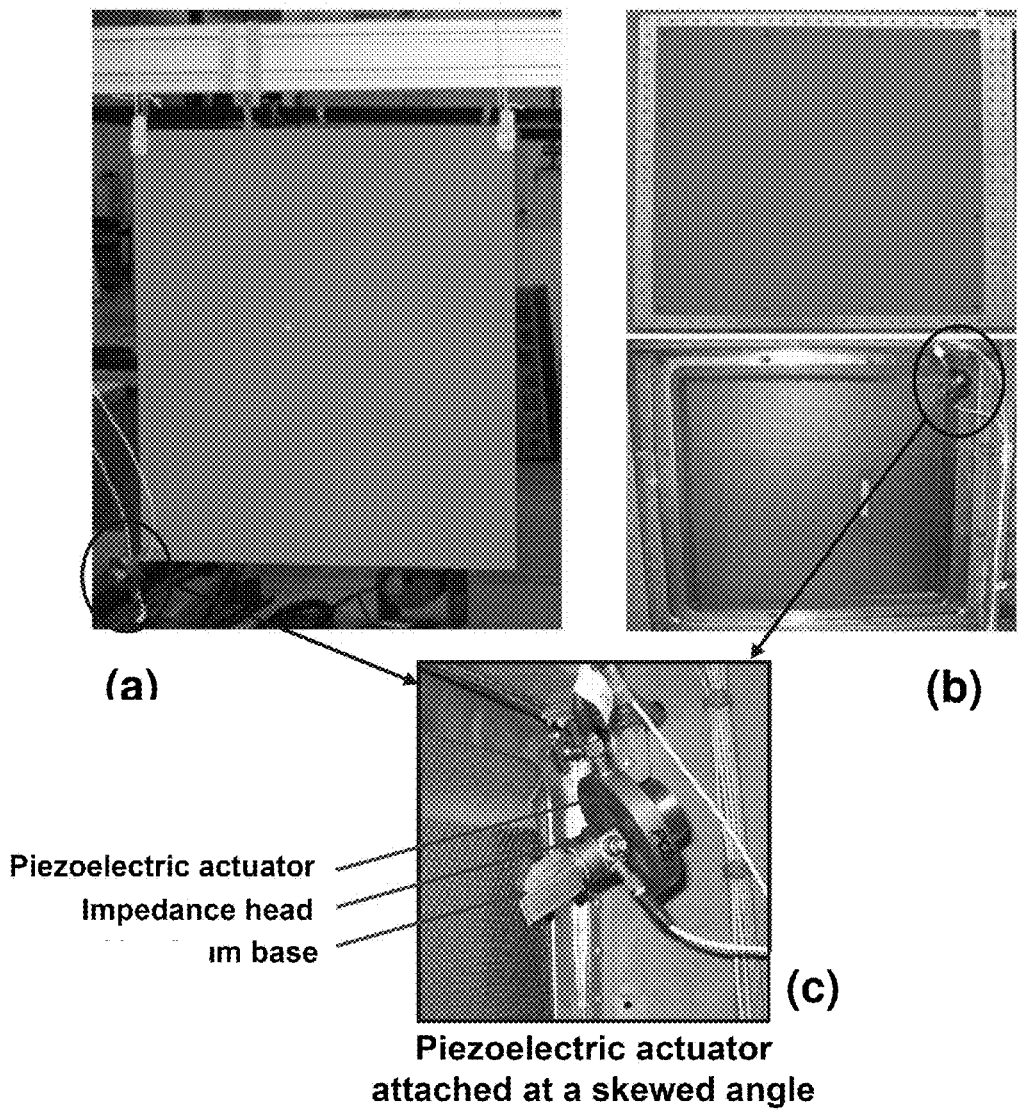

FIG. 12 are photographic representations of (a) a free-free panel, (b) a panel fixed at all edges (showing both sides of the panel, top and bottom), and (c) attachment of a forcing actuator.

Figure 13:
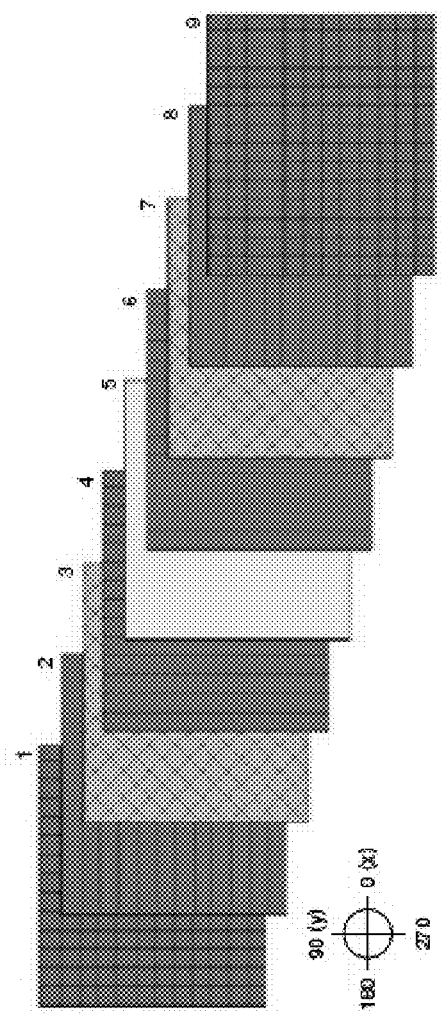

FIG. 13 is a diagram of the panel lay-up for the carbon fiber composite panel.

Figure 14:
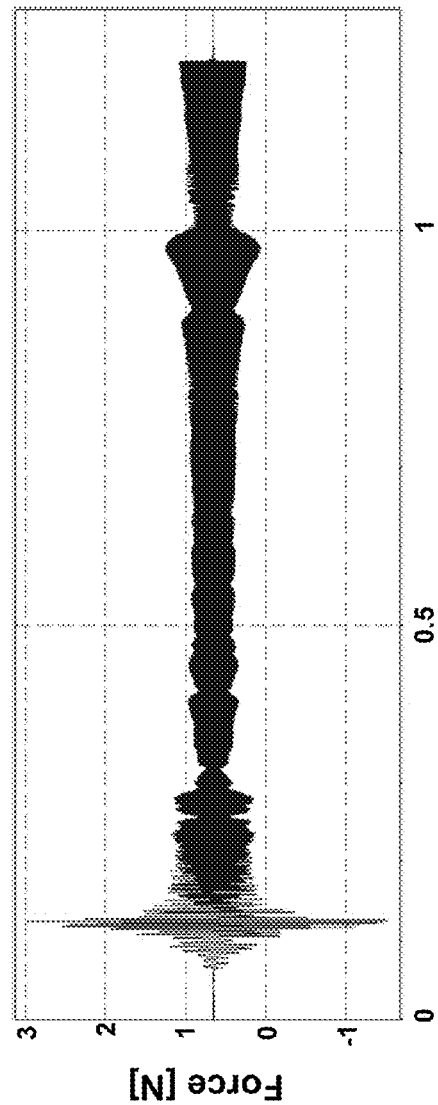

FIG. 14 is a graphical representation of a typical forcing function applied during a frequency sweep.

Figure 15B:
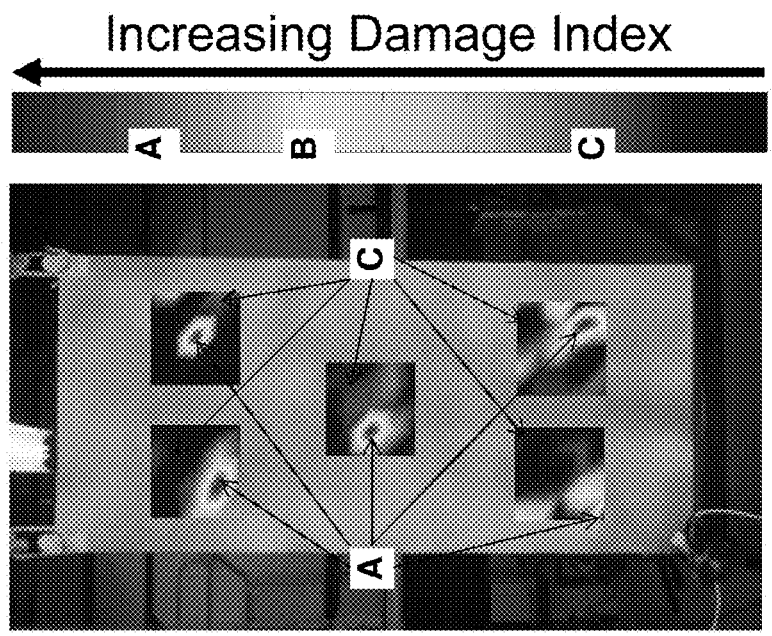

FIG. 15 are schematics showing (a) the impact locations and energies and the corresponding grids used for measurement with the scanning laser vibrometer and (b) the damage index results for each impact location.

Figure 16:
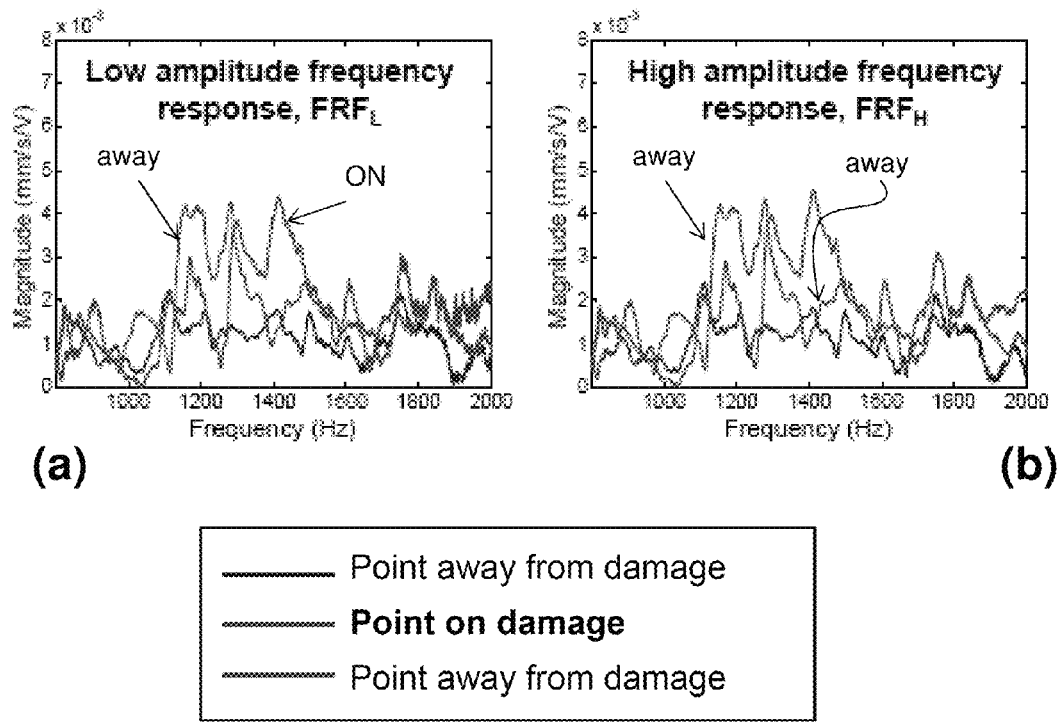
Figure 16:
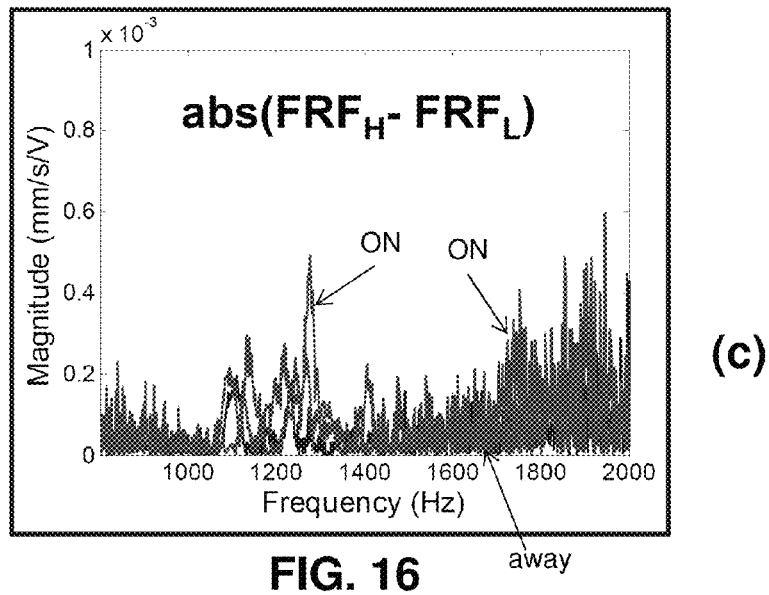

FIG. 16 are graphical representations showing at a particular location on the measurement grid the (a) frequency response with a first forcing function, (b) frequency response at a second forcing function different than the first, and (c) a plot of the absolute value of the difference of the magnitude of the previous two charts as a function of frequency.

Figure 17:
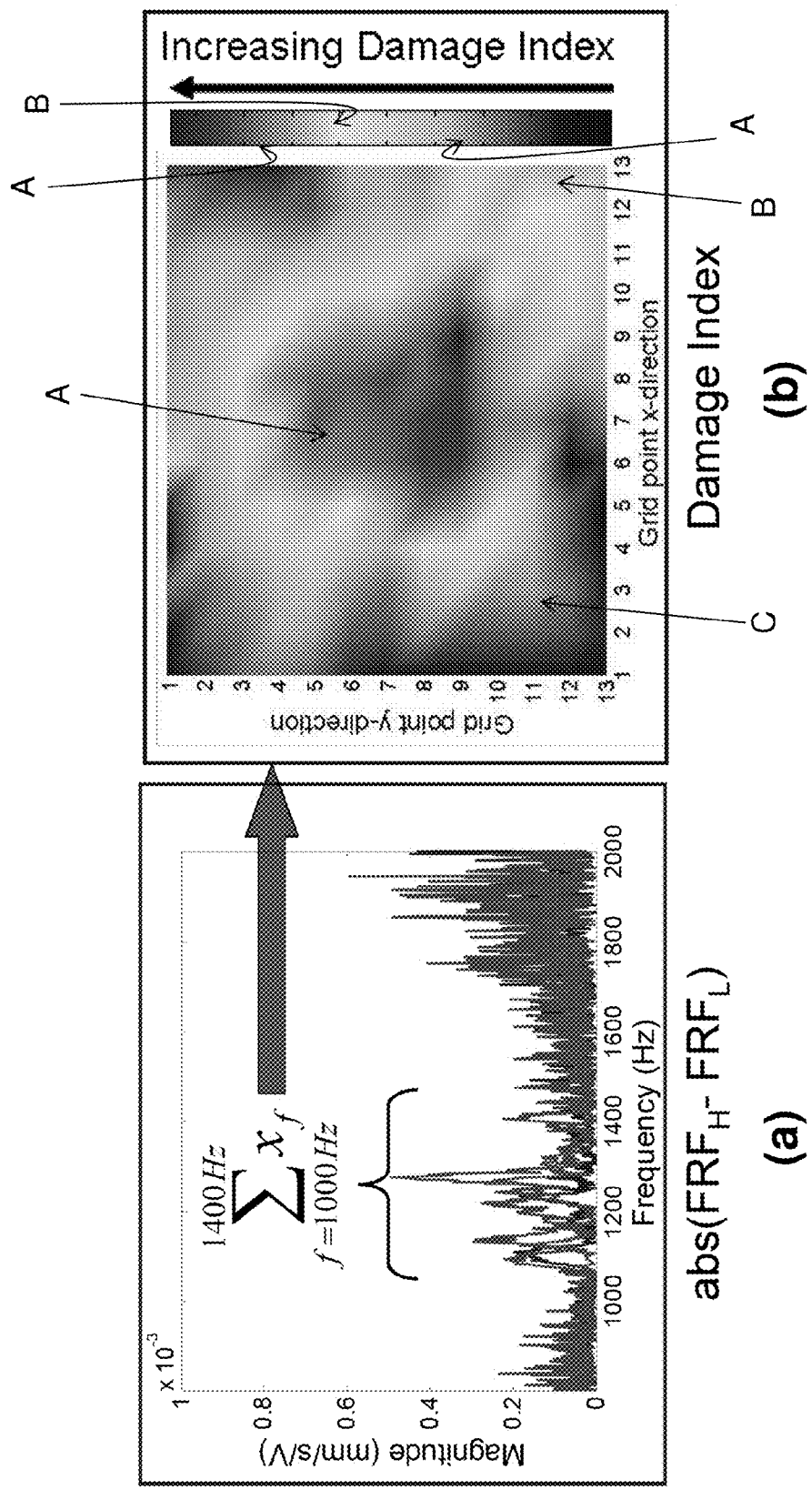

FIG. 17 show (a) a graphical representation of the data of FIGS. 16(a), and (b) a pictorial representation of the damage index in a single direction within a predetermined frequency band.

Figure 18:
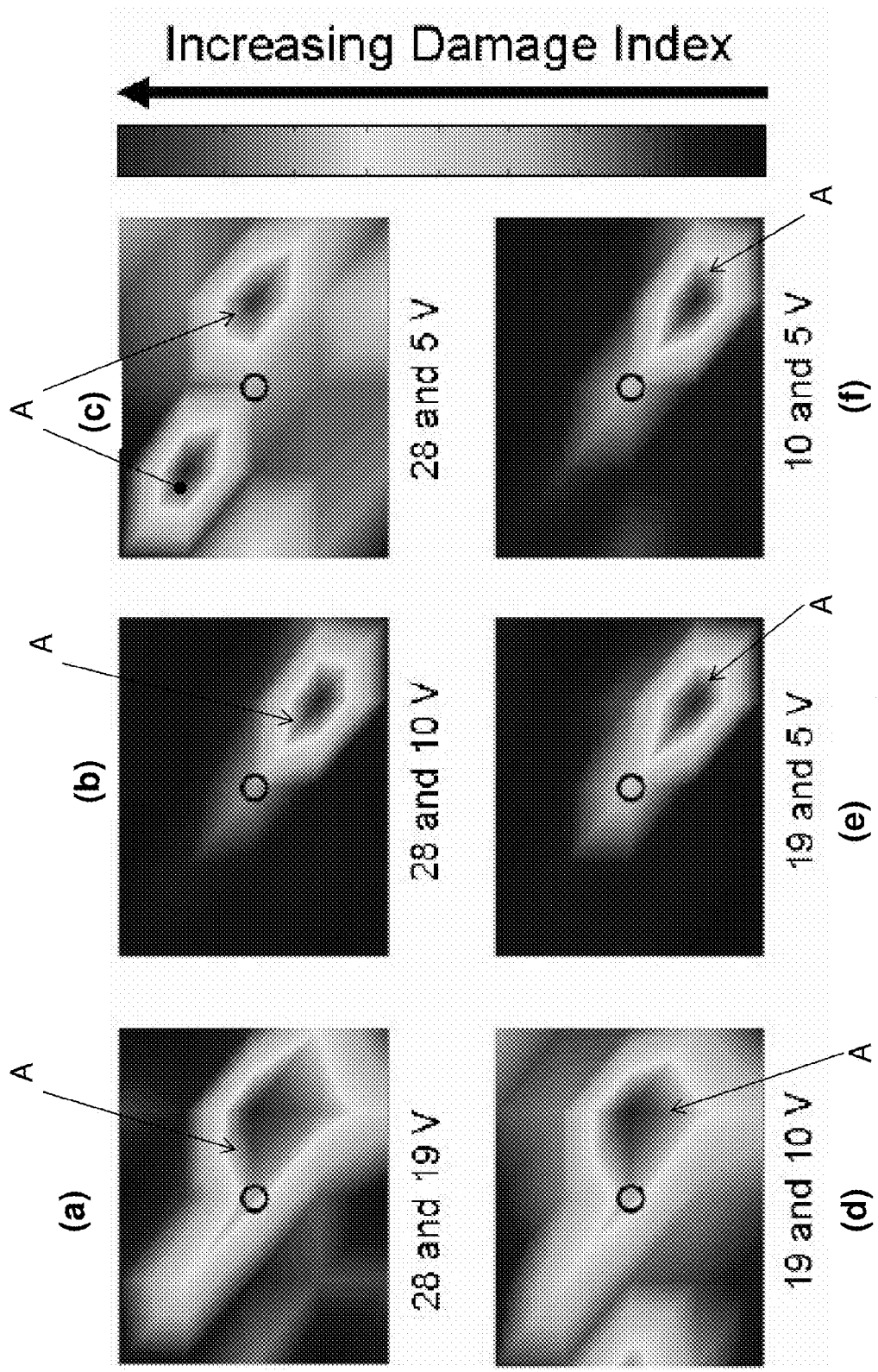

FIG. 18 show pictorial results of an amplitude study performed at the upper 5 ft-lb impact location, showing pictorial representations of damage indices for six different pairs of forcing functions (respectively, a, b, c, d, e, and f).

Figure 19:
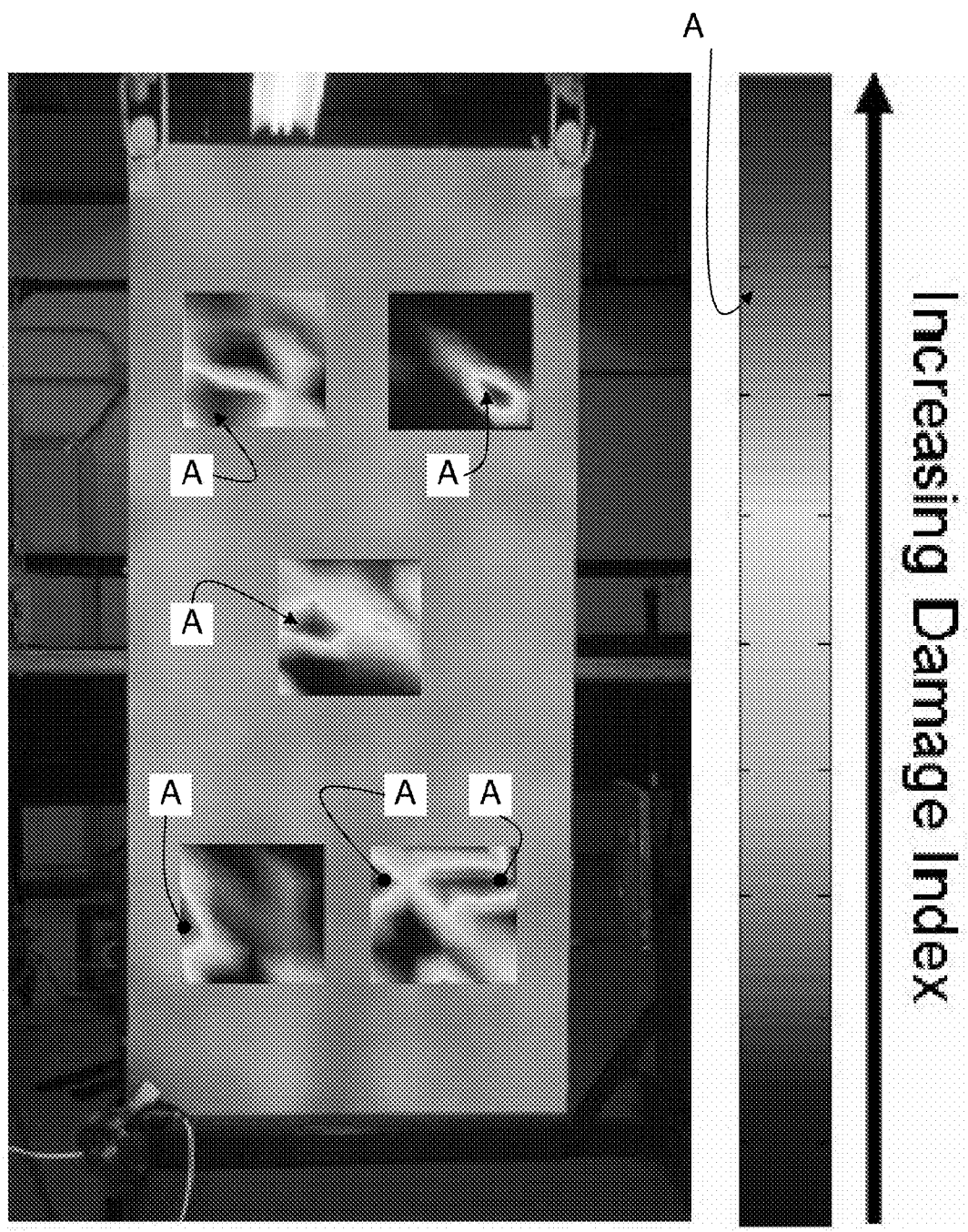

FIG. 19 is a pictorial representation of the damage indices for each impact overlaid on the respective damage locations.

Figure 20:
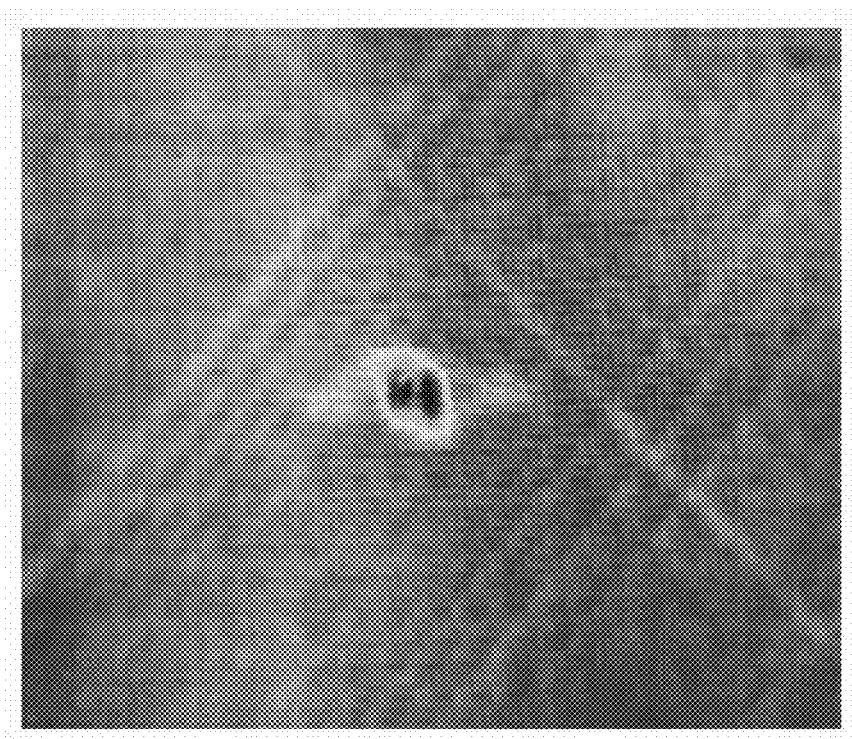
Figure 20:
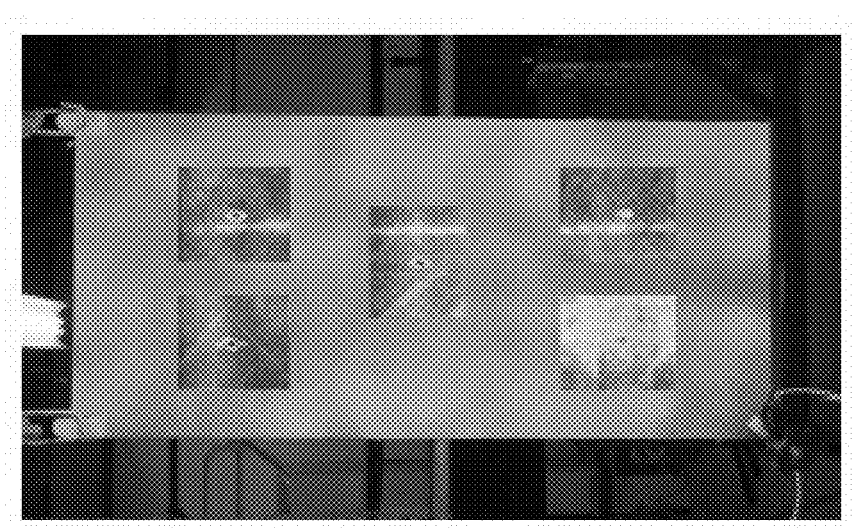

FIG. 20 are thermal images of (a) each of the impact damage locations and (b) the 7 ft-lb impact showing the delamination produced by the impact.

Figure 21:
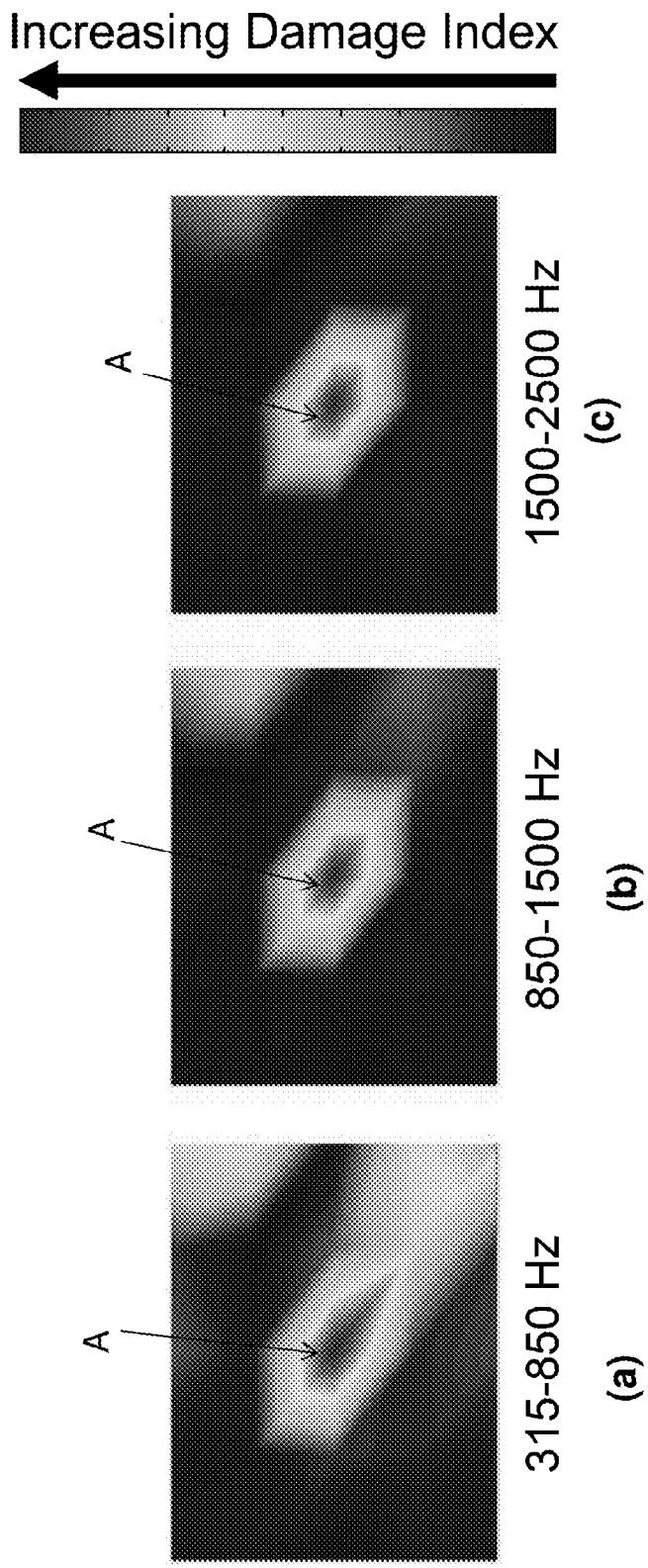

FIG. 21 are damage indices produced at increasingly higher frequency ranges at the upper 5 ft-lb impact location, in three different frequency bands (a, b, and c, respectively).

Figure 22:
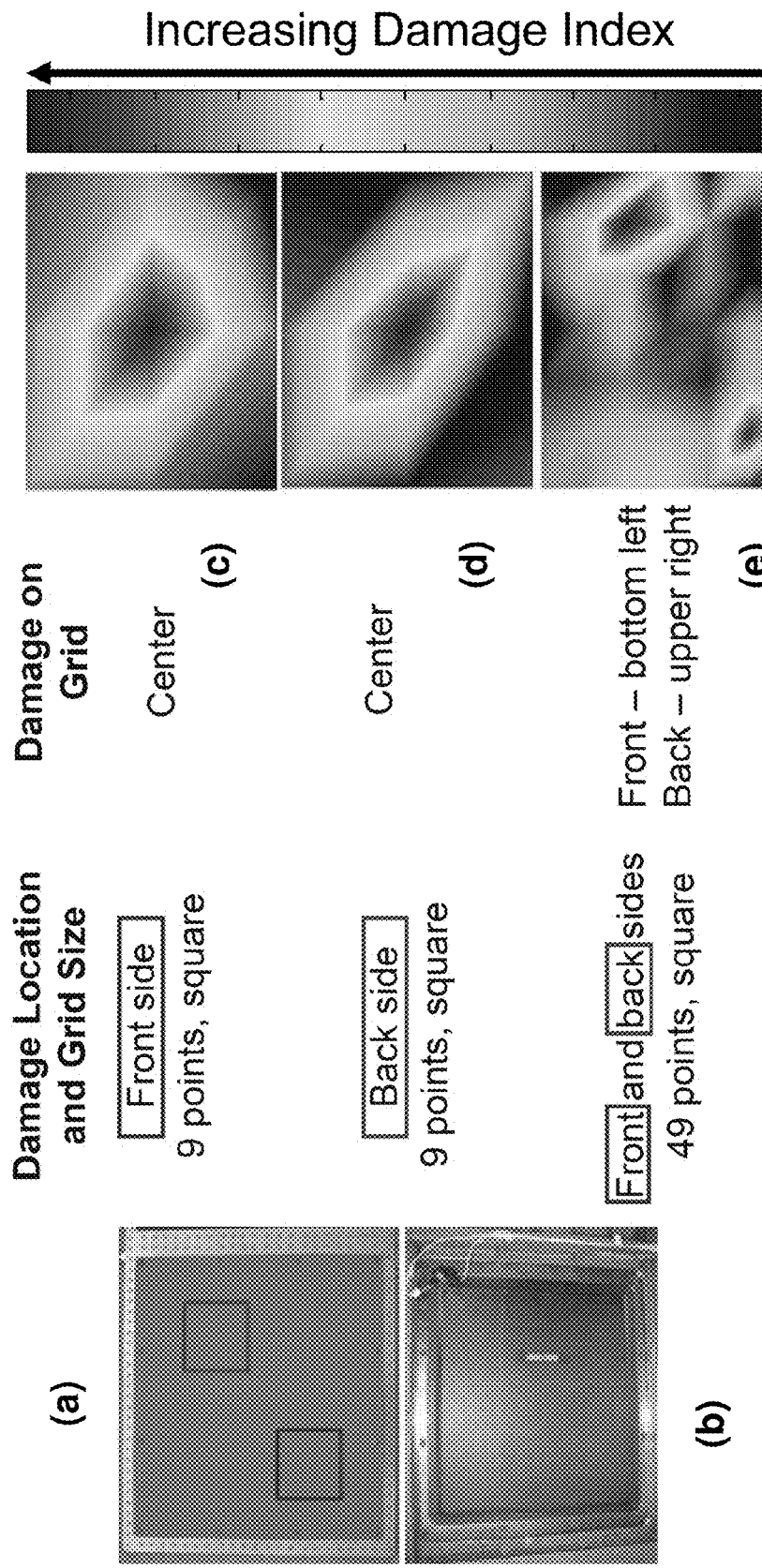

FIG. 22 pertain to experimental results for a panel installed in a rigid frame, showing pictorial representations of the front (a) and back (b), and pictorial representations of damage indices for three cases (c, d, and e, respectively).

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only. Further, with discussion pertaining to a specific composition of matter, that description is by example only, and does not limit the applicability of other species of that composition, nor does it limit the applicability of other compositions unrelated to the cited composition. Some drawings may be described as being "scaled." Such drawings represent a single embodiment of the present invention, and shall not be construed as limiting on other embodiments. However, it appreciated that such drawings may indicate scaling factors that are inventive.

Composite materials are susceptible to subsurface damage mechanisms, which are difficult to detect visually. These damage mechanisms include delaminations, disbonds, and core cracking or crushing. Current inspection techniques used in military aircraft are time consuming and typically require removal of the component for inspection. A robust technique is needed to inspect composite materials for sub-surface damage that addresses these issues. Some embodiments of the present invention pertain to a method that uses a three-dimensional scanning laser vibrometer to measure the forced frequency response of a carbon fiber composite panel as it is excited by a piezoelectric actuator. Analysis of the frequency response functions obtained at varying excitation amplitude levels is performed to identify nonlinear vibration response properties introduced to the panel by material damage. The long-range capability of the scanning laser vibrometer allows for wide-area inspection of a composite specimen, therefore eliminating the need for an aircraft component to be removed for inspection.

Implementation of this vibration-based method has the potential to eliminate the need to remove components from aircraft for inspection by using a long range scanning laser vibrometer to acquire frequency response data. The noncontact measurement technique means that no liquids need to be applied to the test specimen such as in the case of an ultrasound scan, and this vibration method should not be as sensitive to the composition of paint on the specimen as are other surface measurement methods such as thermography. In addition, analysis of frequency response data from two distinct amplitude excitations allows for damage detection without the need for a reference specimen.

Various embodiments of the present invention have shown capable of detecting sub-surface damage by identifying non-linear vibration response characteristics in the frequency response functions measured at various points on subject panels at two distinct excitation amplitudes. In addition, various embodiments allow for improved detection of damage by exciting the test subject at higher frequencies. It is thought that localized damage to the panel can significantly change the localized responses at higher frequencies. Various embodiments are shown capable of detecting damage regardless of the boundary conditions (both free-free and constrained edges being tested), as well as various types of damage, including delamination of laminated panels and core crushing of panels including honeycomb core.

Further, various embodiments show the ability to detect damage on the backside of the panel by measurements taken on the frontside. Yet other embodiments have shown that measurement of the responses of the test subject in three dimensions permits more accurate identification of damaged areas, as compared to measurements taken only in one or two dimensions. However, it is understood that for some types of damage (such as for delamination) acceptable results are produced with two dimensions. Further, it is to be appreciated that in those embodiments utilizing robust techniques of non-linear analysis, data taken in a single direction can be used to adequately detect locations of damage.

Two embodiments of the present invention were verified in actual use. It is understood that these experimentally-validated methods are presented by way of example only, and are not to be construed as limiting to any other embodiments of the present invention.

In a first experimental validation, a measurement method was developed for detecting and locating damage in composite materials by investigating the frequency response behavior of fiberglass sandwich panels subjected to multiple amplitude excitations. The data was analyzed by observing areas of a panel that exhibited strong nonlinear response characteristics. This approach allowed for damage to be located without baseline measurements from an undamaged panel.

Figure 1:
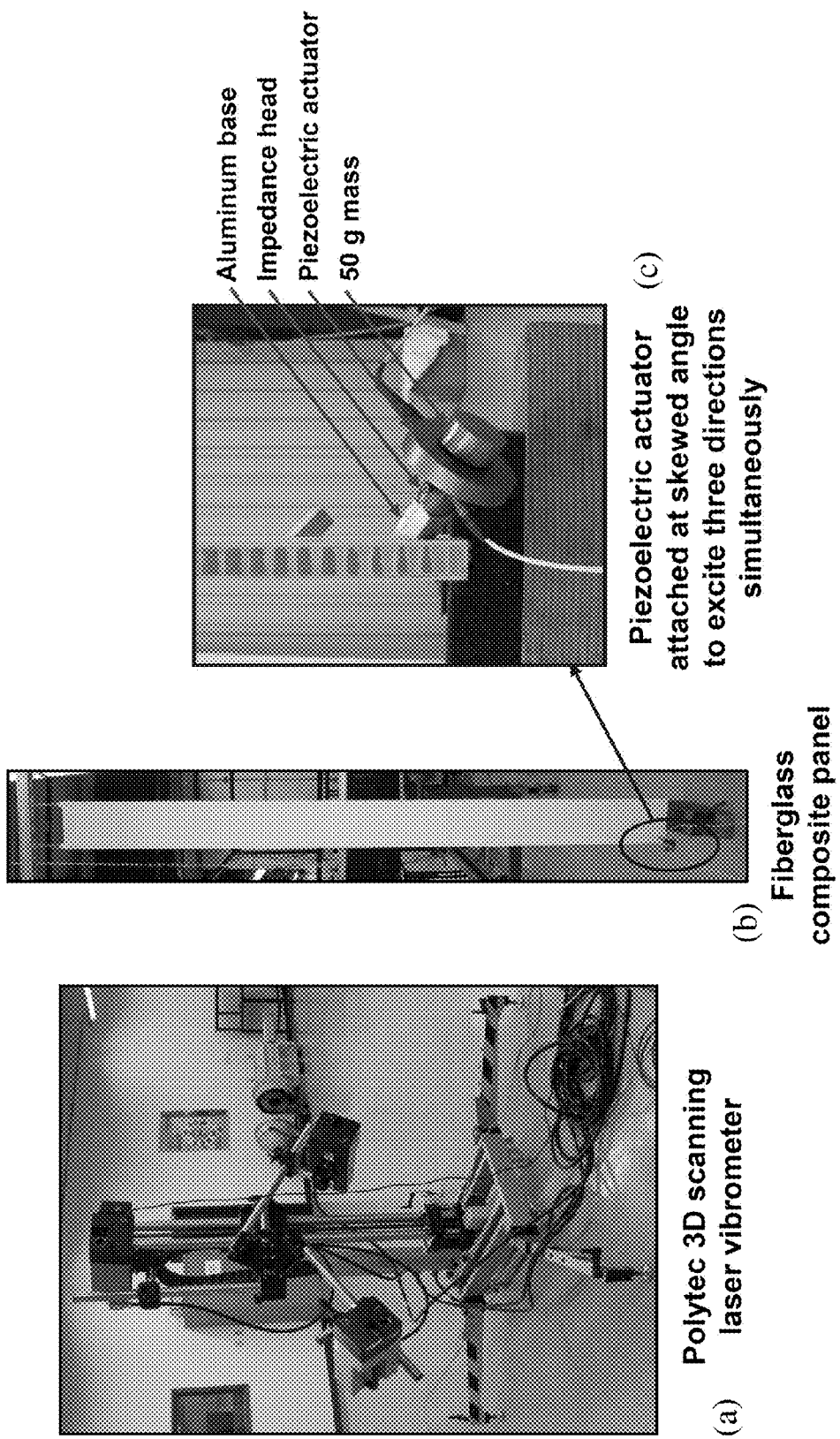
FIG. 1 are photographic representations of the experimental setup, showing (a) the measurement system, (b) the fiberglass panel hung by nylon strings from a free hanging steel bar and (c) the actuator stack attached to the panel at a skewed angle.

Fiberglass panels were chosen for experimental testing because they closely resemble the material used in rotor blade trailing edge structures on military aircraft. A 0.50 in polypropylene honeycomb core with a 10 mm cell size was sandwiched between 0.060 in thick face fiberglass face sheets. A urethane adhesive was used to attach the face sheets to the core. The panels were cut to a length of 7 ft and a width of 6.5 in. The panel being tested was hung by a nylon string from a free hanging steel bar as shown in FIG. 1(a).

A PCB piezoelectric actuator (model 712A02) was screwed into an aluminum block, which was glued to the front side of the panel on the bottom right corner. The aluminum block was attached at a skewed angle in order to excite three directions of response simultaneously. In another example for those embodiments in which a measurement grid has been established on the surface of the specimen being analyzed, the forcing actuator should be coupled into the specimen in such a way that forcing excitation is provided into each of the orthogonal axes established by the measurement grid.

A 50 g mass was attached to the actuator to increase the force input to the panel, and a PCB impedance head (model 288D01) was used to measure the force input applied by the piezoelectric actuator. This setup is shown in FIGS. 1(b) and 1(c).

A Polytec three-dimensional scanning laser vibrometer (model PSV-400) was used to control the actuator input and collect frequency response data for the panel being tested. The surface velocity of the panel was measured in three orthogonal directions and compared with the force measured through the impedance head. A frequency response function between these two measurements was saved for each of the transverse, lateral, and longitudinal directions. Although what has been shown and described is the use of a laser vibrometer for measurement of velocity data, it is understood that other embodiments of the present invention are not so constrained, and include the use of any type of movement data, including position or acceleration. Further, although what has been shown and described is the use of three-dimensional data, it is understood that this is by way of example only. Yet other embodiments of the present invention include the use of two-dimensional data or one-dimensional data.

Figure 2C:
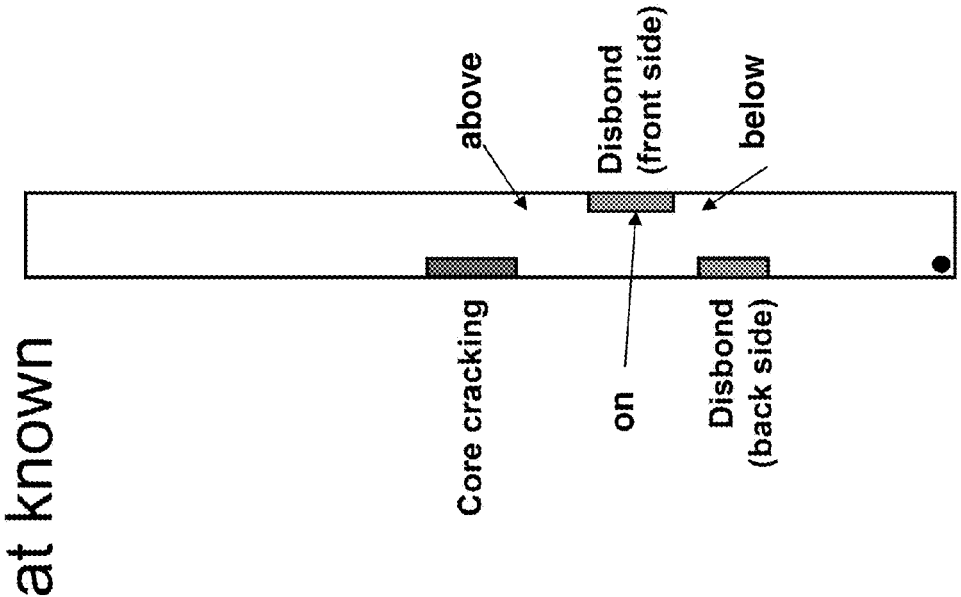
FIG. 2(c) is a schematic of damage mechanisms and locations on a fiberglass panel.
Figure 2C:
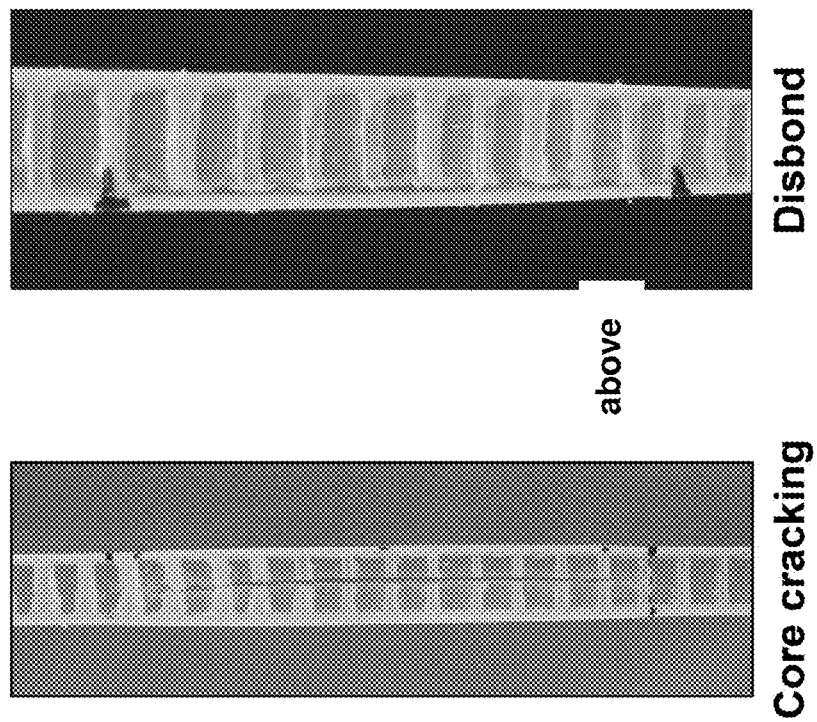

A fiberglass panel was damaged at several locations as shown in FIG. 2(c). A core damage location was investigated as well as two disbond damage locations. One of the disbonds was between the front face sheet and the honeycomb core (front side), and the other disbond was between the back face sheet and the honeycomb core (backside). Each of these damage mechanisms was introduced to the panel by creating a cut of known length at the damage location. The core damage was approximately 5 inches in length. Each of the disbond damages were 4 inches in length and were created by placing a cut in the urethane adhesive, causing the face sheet to separate from the honeycomb core. FIGS. 2(a) and 2(b) show core damage and disbond damage mechanisms, respectively.

For each test performed, a grid was created on the panel in the vicinity of the damaged region being investigated using the laser vibrometer software. The input voltage supplied to the actuator was a sine sweep excitation from 100 to 5000 Hz over a sample time of 1.28 s. Twenty-five averages were collected for each point on the defined grid. Two datasets were collected for each test performed, one at a low amplitude excitation of 21.3 V and one at a high amplitude excitation of 28.4 V.

The frequency response functions collected through the laser vibrometer were used to detect the damage with an assumption that composite material damage introduces non-linear stiffness and/or damping properties in the material at the damage location. These nonlinearities may be observed by comparing the frequency response functions from two distinct amplitude excitations. For the experiments performed here, it is expected that damaged regions of the panel will exhibit larger changes than undamaged regions of the panel when this comparison is made. It is possible that the undamaged regions will react to a change in forcing function in a generally linearly manner. However, the damaged regions will provide a response that is substantially different than that of the undamaged regions, and in particular exhibit a nonlinear response. As one example, an undamaged region of the panel may respond to an X percent increase in excitation force with an increase in surface velocity of X percent. However, other regions the response of the panel may be Y percent, such that the value of Y is substantially different than the value X. This change could be due to a localized change in damping, stiffness, or effective mass resulting from the damage.

Analysis of the input force to the panel showed that the actuator had a limited force range over which its forcing excitation was approximately flat. In order to avoid discrepancies between a change in the input force level as a function of frequency and a nonlinear response due to damage, only this flat range of the actuator extending from 315 to 850 Hz was considered for investigating material damage (referred to as the frequency range of interest). However, it is understood that other embodiments of the present invention do not include this limitation on the forcing range of the actuator. Some of those other embodiments utilize a load cell placed inbetween the actuator and the panel to directly measure the force being applied.

The ordinary coherence between the input and output was observed for all measurements made. This coherence was near unity for the frequency range of interest, indicating that the outputs were linearly correlated with the actuator input.

Figure 3:
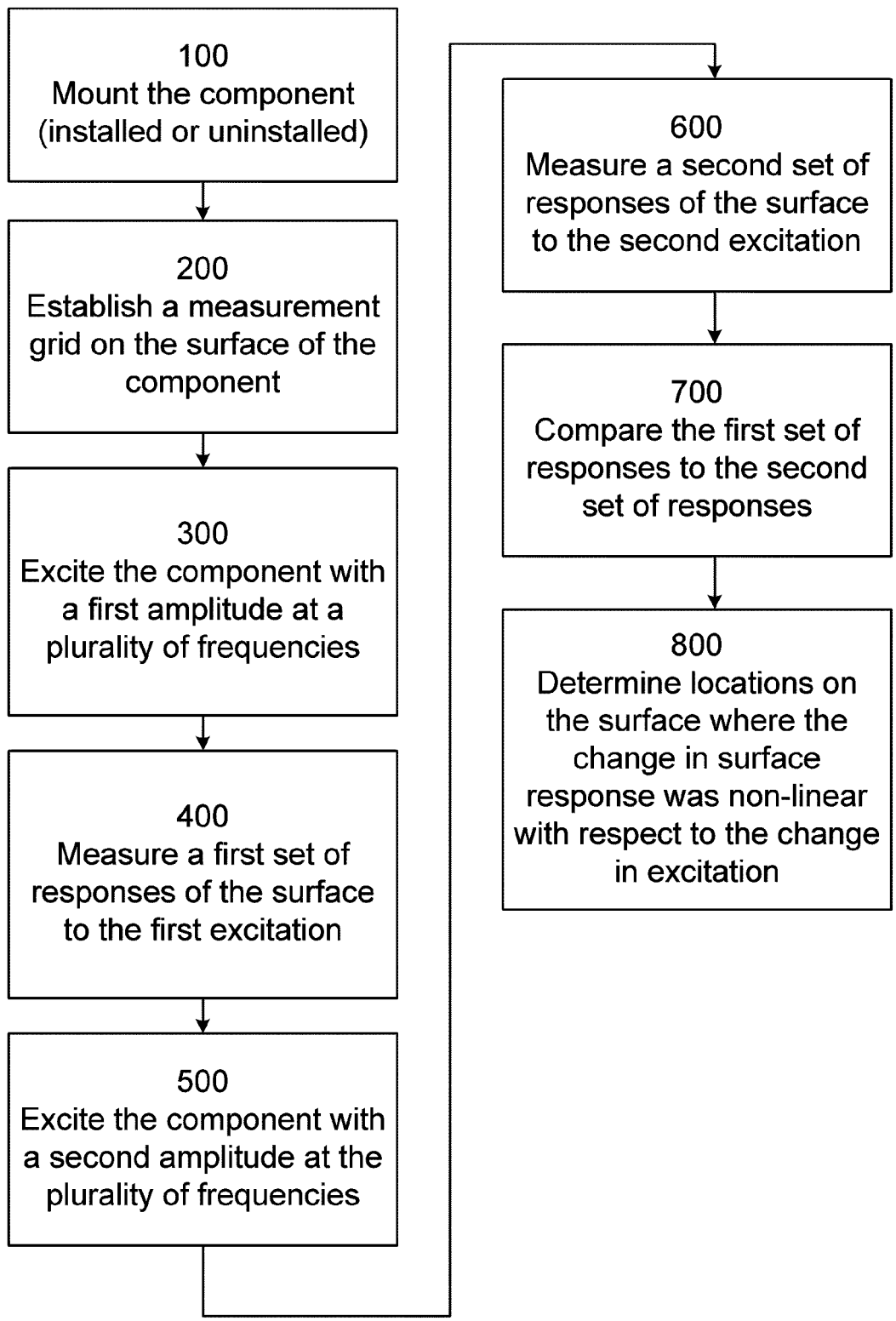
FIG. 3 is a block diagram of a method according to one embodiment of the present invention.

FIG. 3 shows a method for determining the structural integrity of a panel according to one embodiment of the present invention. The method include mounting 100 a component to the analyzed. In some embodiments, the component is a panel, which can be any type of panel, including laminated panels and panels including honeycomb cores. However, it is appreciated that other embodiments of the present invention pertain to any type of device.

The component can be mounted in any manner, including mounting in a test rig, and also including the normal mounting of the component as it is used. As one example, the component can be a panel that is part of the primary structure of an aircraft. As another example, the component can be a blade of a helicopter, which can remain installed on the mast.

Further, some embodiments include performing the vibratory excitation while the component is still integrated into the larger structure. For example, in those embodiments in which the component is a panel, the panel may still be riveted into a vehicle (such as an air vehicle or a road vehicle). Further, the integrated panel may include other components mounted to it, including, for example, air data sensors (on the exterior of an air vehicle) or door handles or brackets (on the interior). However, the present invention also contemplates those embodiments in which the integration of the component to be tested is only partial. For example, one or more rivets or other fasteners may be removed or only partly fastened. An exterior component may be removed completely or partly. An interior component such as a door handle or a bracket may be removed, or the device mounted to the bracket may be removed. Therefore, it is understood that the integrated component may be fully integrated, or only partly integrated into the larger assembly.

The method also includes establishing 200 a measurement grid on the surface of the component. Preferably, the measurement grid has sufficient fineness to locate damage in the component that is above some predetermined minimum value of damage. Further, the grid preferably is coarser in those areas where the user has determined that the likelihood of damage is low. In some embodiments, the measurement grid is equidistant and rectangular, but any type of measurement grid is contemplated. Further, yet other embodiments contemplate vibration testing and measurement at only a single point.

The method further includes exciting 300 the component with a first forcing amplitude at a plurality of frequencies. In some embodiments, the excitation is mechanical, and further includes an actuator that is mechanically linked to the component. However, other embodiments contemplate other types of excitation, including sinusoidal and random vibration and acoustic excitation as examples.

Preferably, the component is excited with an amplitude that would otherwise result in linear elastic behavior of the component. For example, the excitation is preferably not so excessive as to inelastically deform the component. Further, it is preferred that the excitation be applied at a plurality of frequencies over a predetermined range of frequencies. As will be discussed later, the various damage indices may be more apparent in some frequency ranges than others. For this reason, it is preferably to excite the component over a range of frequencies that will encompass these specific frequency bands at best show damage.

The method further includes measuring 400 the responses of the surface to the first excitation. The measured responses are preferably spatial in nature, such as position, velocity, or acceleration. Although what will be shown and described herein is measurement of surface velocity, yet other embodiments contemplate use of positional or acceleration data, dependent upon the geometry of the component being tested, the nature of the excitation, the nature of the expected damage, and related factors.

In addition, some embodiments contemplate measuring the spatial characteristics of each point in three orthogonal directions. It has been found that some types of damage exhibit relatively little response along a particular measurement axis, but enhanced response in a direction orthogonal to that axis. However, other embodiments contemplate the measurement of one dimensional or two dimensional responses.

The method further includes exciting 500 the component at a second, different amplitude over the same range of frequencies. This second excitation amplitude can be greater than or less than the first amplitude. The method further includes measuring 600 a second set of responses of the surface to the second excitation.

The method further includes comparing 700 the first set of responses to the second set of responses. Preferably, the first set of positional responses is normalized by a factor relating to the first amplitude (for example, the factor can be related to the forcing function in Newtons, or for an electric actuator with a linear range, volts). Likewise, the second set of responses is normalized to the second amplitude. In one embodiment, the comparison further includes calculating the absolute value of the difference between the first set of responses and the second set of responses, including for each point and further for each axis of measurement.

The method further includes determining 800 locations on the surface where the change in surface response was nonlinear with respect to the change in excitation. These locations can be determined by a variety of assessment methods, including any of the following. In some embodiments the method includes analyzing the first data and the second data using a coherence function. In other embodiments, the vibration is random and the method includes analyzing the first data and the second data using a bispectra technique. In still other embodiments, the vibrating is sinusoidally swept vibration and the method includes analyzing the first data and the second data by the method of restoring forces. In other embodiments, the method includes analyzing the first data and the second data using autoregressive exogenous input frequency models. In yet other embodiments, the method includes analyzing the first data and the second data using transmissibility functions. In some embodiments, the method includes analyzing the first data and the second data by nonlinear identification through feedback of the outputs. In some embodiments the method includes analyzing the first data and the second data by vibro-acoustic modulation. It is understood that some of the foregoing techniques do not require two datasets, as will be apparent to one of ordinary skill in the art.

Figure 4A:
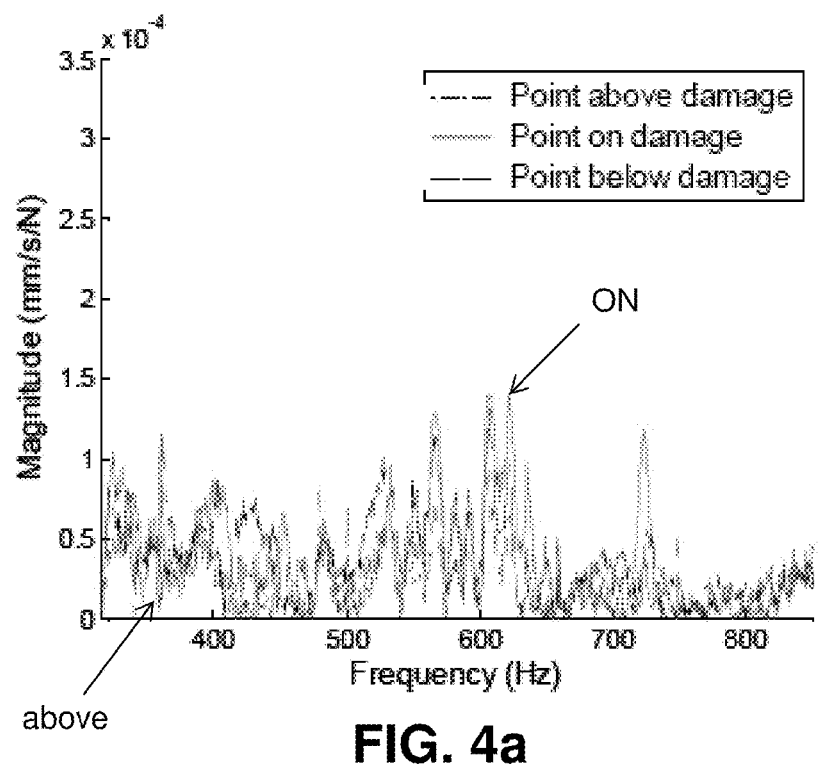
FIG. 4 are graphical representations showing (a) a comparison of the frequency response functions for the core damage location for the frequency range of interest, and (b) a smaller frequency range for illustration purposes.
Figure 4B:
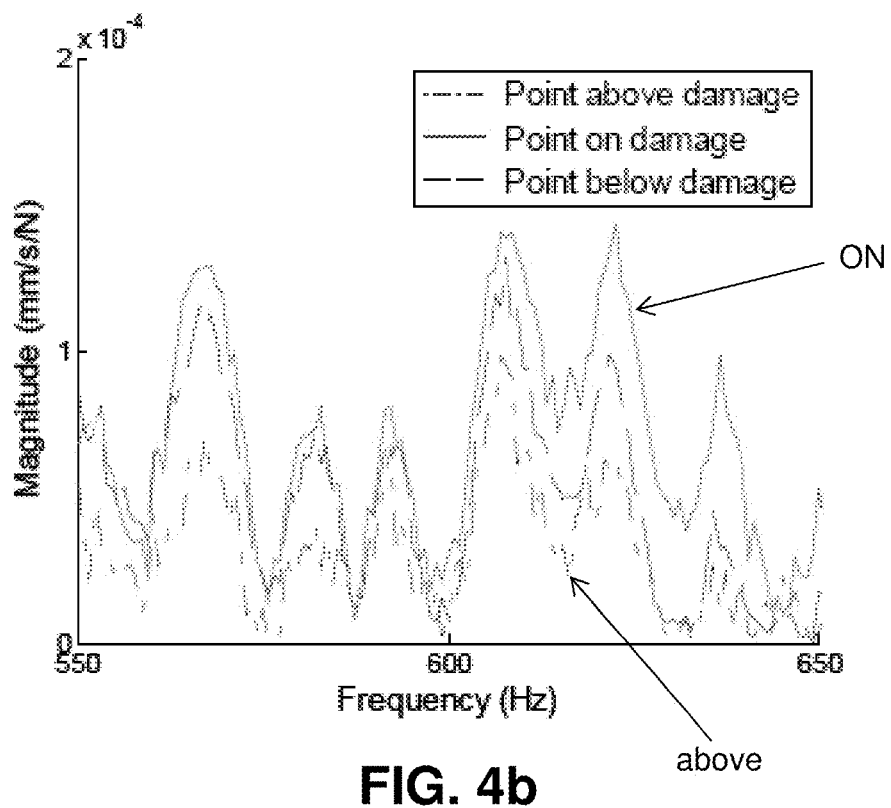

Reference is now made again to the first experimental validation of the method thus described. Comparison of the frequency response functions from the high and low amplitude datasets was investigated by computing the absolute value of the difference between the two frequency response functions. FIG. 2(c) shows a schematic of several points used in this comparison for the core damage location including a point above, a point on, and a point below the damage location. FIG. 4(a) shows the comparison for a frequency range of interest, while FIG. 4(b) shows a reduced frequency range that is about one octave for illustration purposes. The results shown are for the transverse direction (out of plane) measurements, although the trends observed are similar in both the lateral as well as longitudinal directions. FIGS. 4, 5, and 6 show comparisons that are the difference between the high and low amplitude frequency response functions (i.e., the difference between the frequency response functions of the two datasets at the two different forcing amplitudes).

As seen in FIGS. 4(a) and (b), the point located on the damage location (represented by the solid line) exhibits the largest change in the corresponding frequency response function when the panel is excited at two amplitudes. For most of the data collected, a trend was seen for the points not located on a damaged region of the panel, where the magnitude of this difference increased as the points approached the actuator. In damaged regions of the panel, the magnitude of this difference does not follow the same trend, but displays an disproportionately higher magnitude difference. Using this information, the damage was detected by identifying this nonlinear behavior in the forced frequency response of the panel. It is noted, however, that this behavior is not consistent throughout the entire frequency range displayed. Instead, there are specific frequency ranges where the nonlinear response is apparent.

Figure 5A:
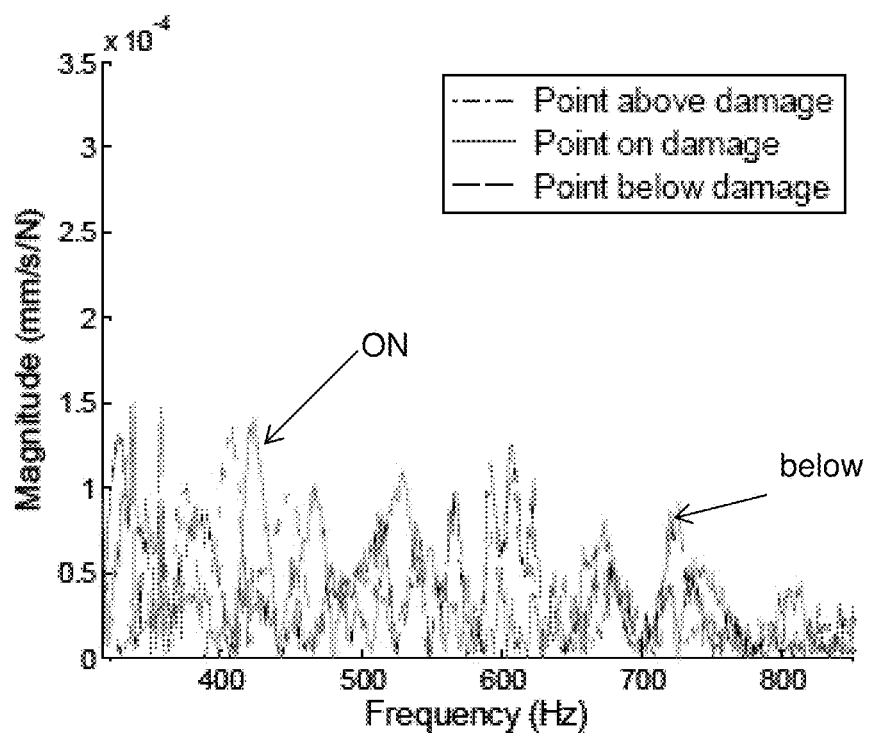
FIG. 5 are graphical representations showing a comparison of the frequency response functions for (a) the disbond damage on the front side of the panel and (b) the disbond damage on the back side of the panel.
Figure 5B:
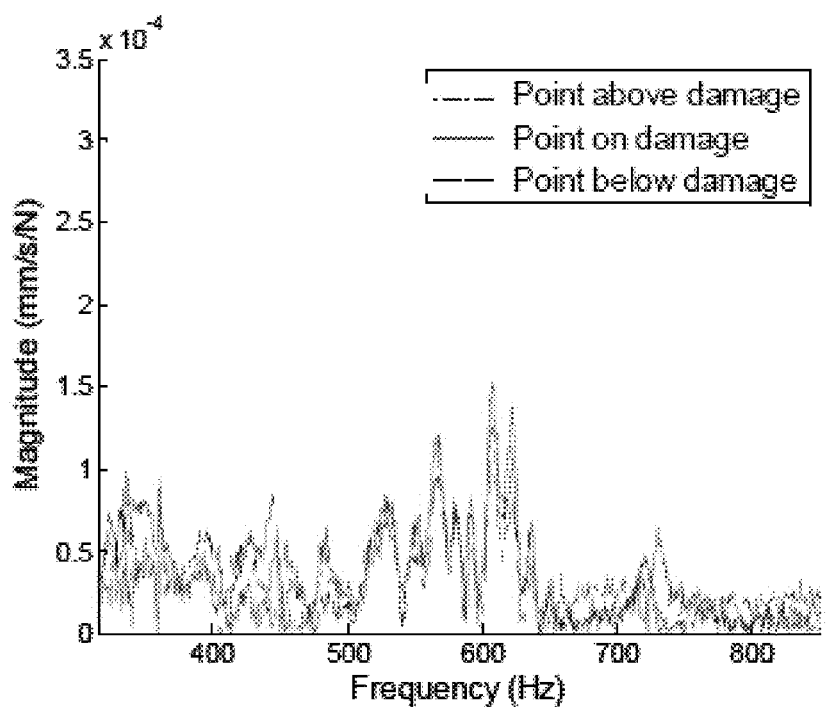
Figure 6:
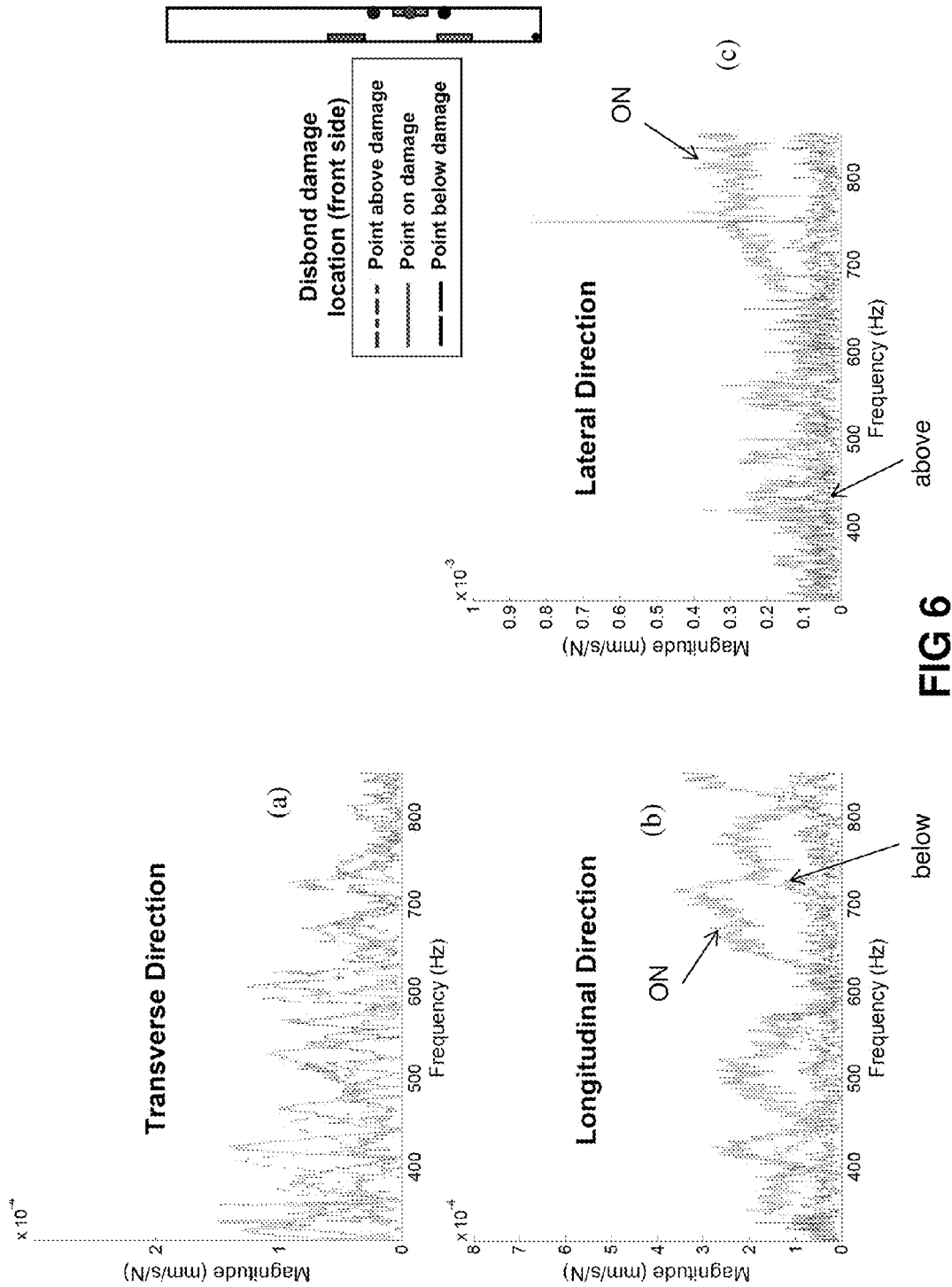
FIG. 6 are graphical representations of the comparison of the frequency response functions for disbond damage in (a) to transverse direction, (b) the longitudinal direction, and (c) the lateral direction.

Similar results are seen for the disbond damage locations on both the front and back sides of the panel, as seen in FIGS. 5(a) and (b), respectively. Each of the damage mechanisms investigated here displayed different properties when the difference between the two frequency response functions was compared. However, they displayed the same general trend in which regions of the panel exhibiting the most pronounced nonlinear response lay directly on the damage location. Although the frequency ranges where this trend was apparent varied for each damage location, this information may be useful in determining which damage mechanism has been detected. In addition, the nature of the comparison between the two frequency response functions may also be used to determine the location of the damage in relation to the excitation source thereby providing a second means of locating the damage.

Analysis of the data displayed in FIG. 4(a) and FIGS. 5(a) and (b) suggests that different frequency ranges can be used when determining damage locations depending on the damage mechanism being investigated. By picking the frequency ranges where the trends discussed here are most apparent, a damage index may be computed for each damage location by computing the sum of the difference across the chosen frequency ranges.

FIGS. 6(a), 6(b), and 6(c) show data similar to that presented for FIGS. 4 and 5, as measured at the frontside disbond site at points above the damage, on the damage, and below the damage. It can be seen that measurements at all three points in the transverse direction show relatively view distinct peaks, even for measurements taken at the damaged location. In contrast, measurements in the longitudinal direction show several peaks spanning the octave from 400 Hz to 800 Hz. Velocity measurements made in the lateral direction show a substantial difference in response above 700 Hz. These three plots show that it is helpful to make velocity measurements in three orthogonal axes, and further to prepare damage indices that reflect information from all three axes. As can be seen in FIG. 6(a), for some types of damage and with some damage indices, if the damage indices were based only on a single direction, it is possible to make a significant error in assessing the location, quantity, or even existence of damage.

It is seen from the forced frequency response data that the damage mechanisms investigated, including core damage, disbond damage on the front side of the panel, and disbond damage on the back side of the panel, all displayed nonlinear mechanical characteristics when comparing the frequency response functions produced by a sine sweep excitation at two distinct amplitudes. These nonlinear characteristics were highlighted by computing the absolute value of the difference between the two frequency response functions. A summation of the magnitude of these differences over the frequency ranges where the trends previously discussed were apparent was used to create a damage index for each damage location investigated. To increase the sensitivity of the damage indices created for each damage location, the product of the summation results for the transverse, lateral, and longitudinal directions was computed, thereby creating a new index that accounts for the coupling between the measurement directions. It is understood that the damage index can be created with information from fewer than all of the three orthogonal directions. For example, some types of damage may result in responses that are most prominent in one or two dimensions, and in such cases the damage index is correspondingly simplified. Further, it is understood that a device that is suspected of being damaged (such as the panel) can be analyzed with different types of damage indices, each one adapted and configured to show different types of damage (core damage, disbond damage, etc.).

Figure 7:
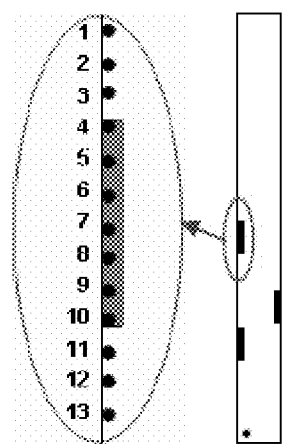
FIG. 7 depict a point numbering system referred to in FIGS. 8 and 9 for the (a) core damage, (b) rear disbond damage and (c) front disbond damage.
Figure 7:
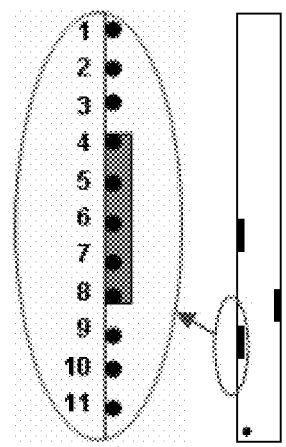
Figure 7:
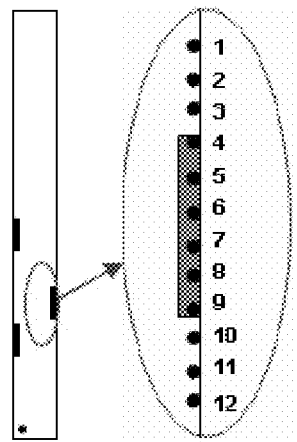

FIGS. 7(a), (b), and (c) show schematics of each of the damage locations investigated (core damage, disbond damage on the back side of the panel, and disbond damage on the front side of the panel, respectively) and the point numbers used in developing appropriate damage indices for each case.

FIG. 8 shows an example of the effect that each of the transverse, lateral, and longitudinal directions has on the resulting damage index. The case shown is for the disbond damage on the front side of the panel, where FIGS. 8(a), (b), and (c) show the damage indices created for the transverse, lateral and longitudinal directions, respectively, and FIG. 8(d) shows the final damage index computed by taking the product of the three directions.

Figure 8A:
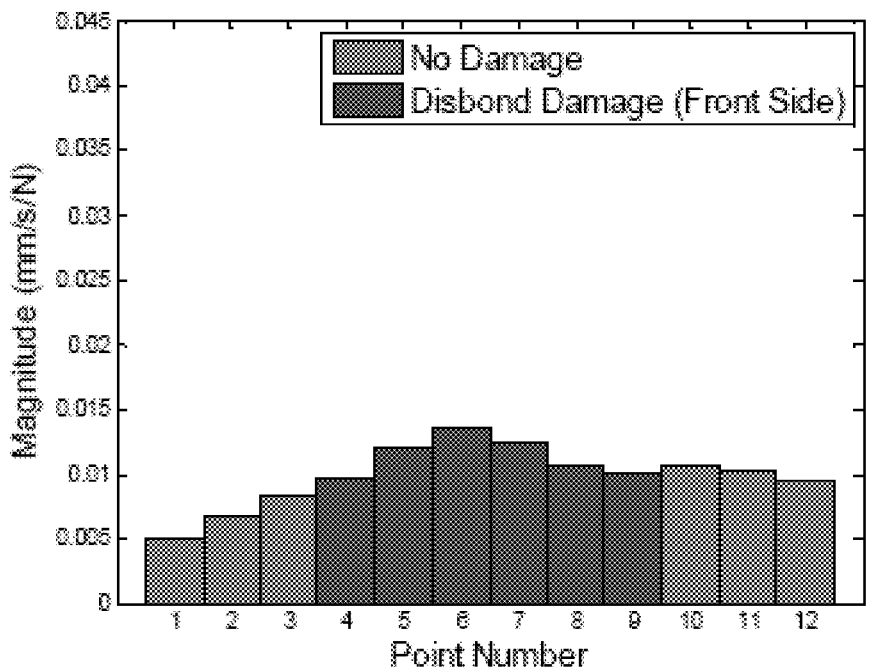
FIG. 8 are graphical representations showing the results of computing the summation of the magnitude difference between the frequency response functions from the disbond damage location on the front side of the panel in (a) the transverse direction, (b) the lateral direction, (c) the longitudinal directions, and (d) the product of all three directions. (Refer to the numbering system in FIG. 7.)
Figure 8B:
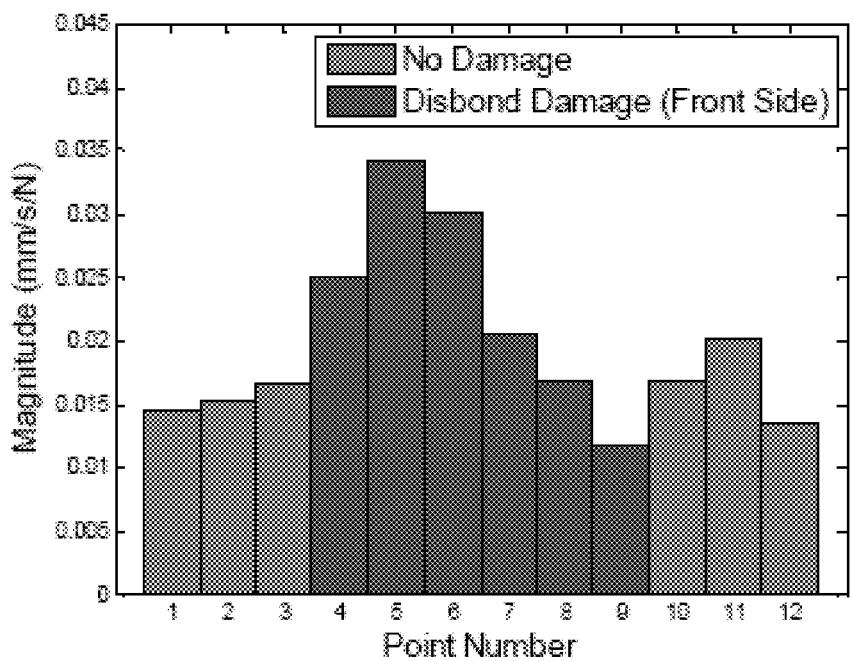
Figure 8C:
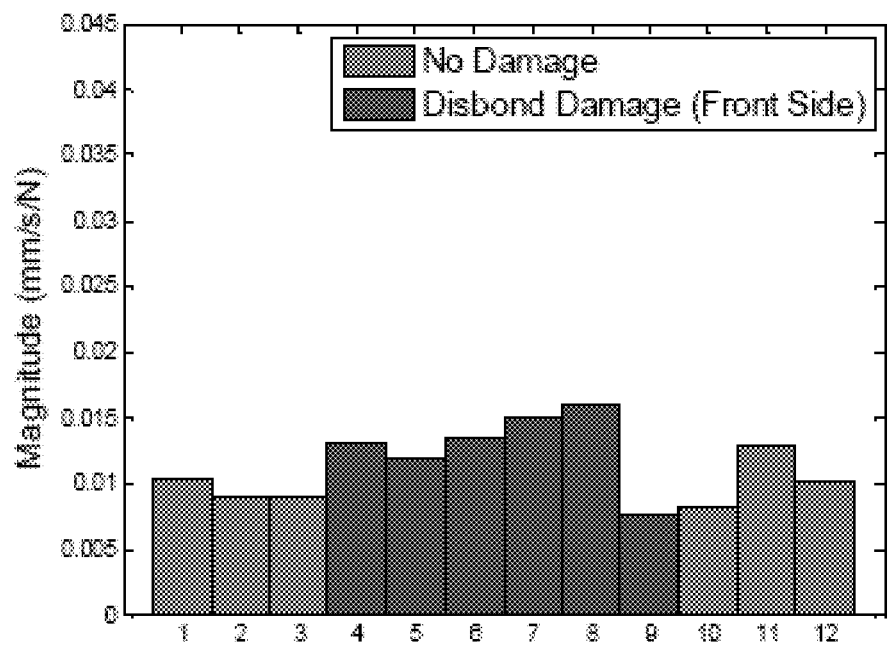
Figure 8D:
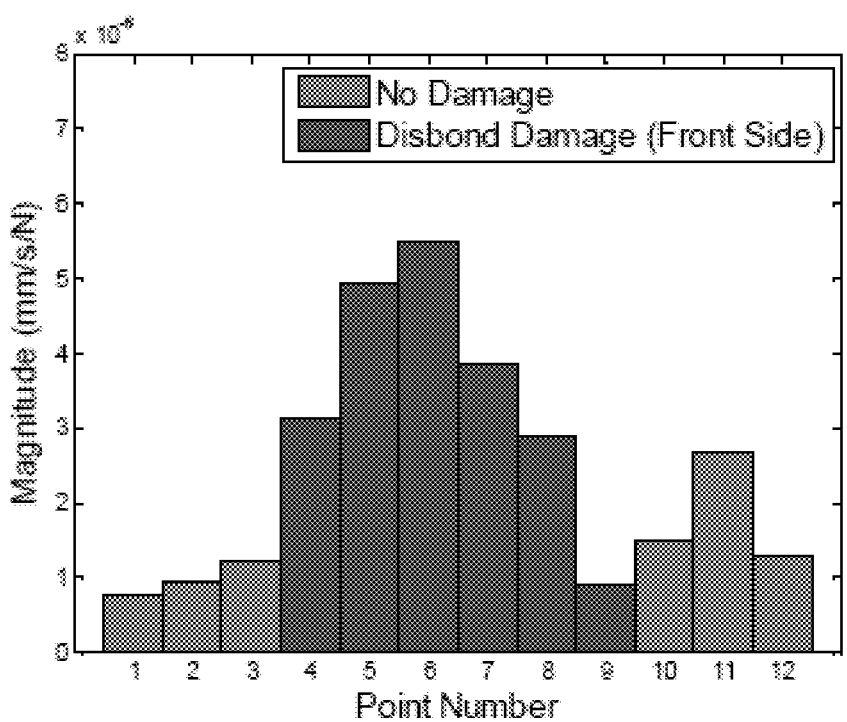

As seen in FIG. 8, each of the individual damage indices created had an influence on the final damage index in FIG. 8(d). The combination of the three directions together helped to create a more sensitive final damage index by allowing for amplification of the nonlinearities caused by material damage. The end result gives an indication of where damage is located. This behavior shows one aspect of using the three-dimensional laser vibrometer as opposed to a one-dimensional system. With the three-dimensional capability, it is possible to more accurately locate small levels of damage by considering coupling between measurement channels.

Figure 9A:
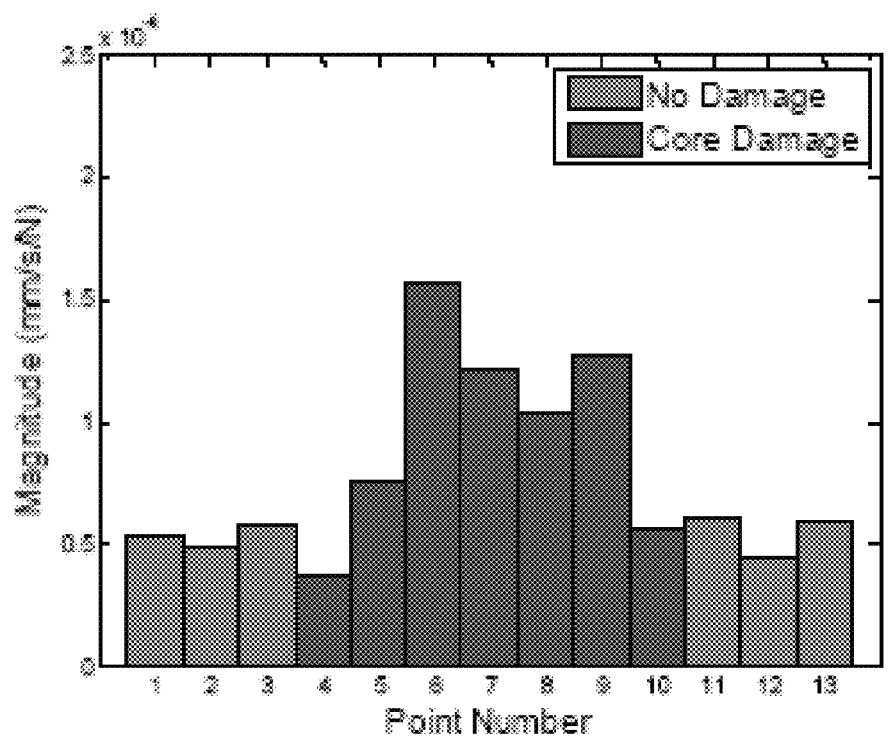
FIG. 9 are graphical representations showing the damage indices created for (a) the core damage location and (b) the disbond damage on the back side of the panel by computing the product of the summation results for the transverse, lateral, and longitudinal directions. (Refer to the numbering system in FIG. 7.)
Figure 9B:
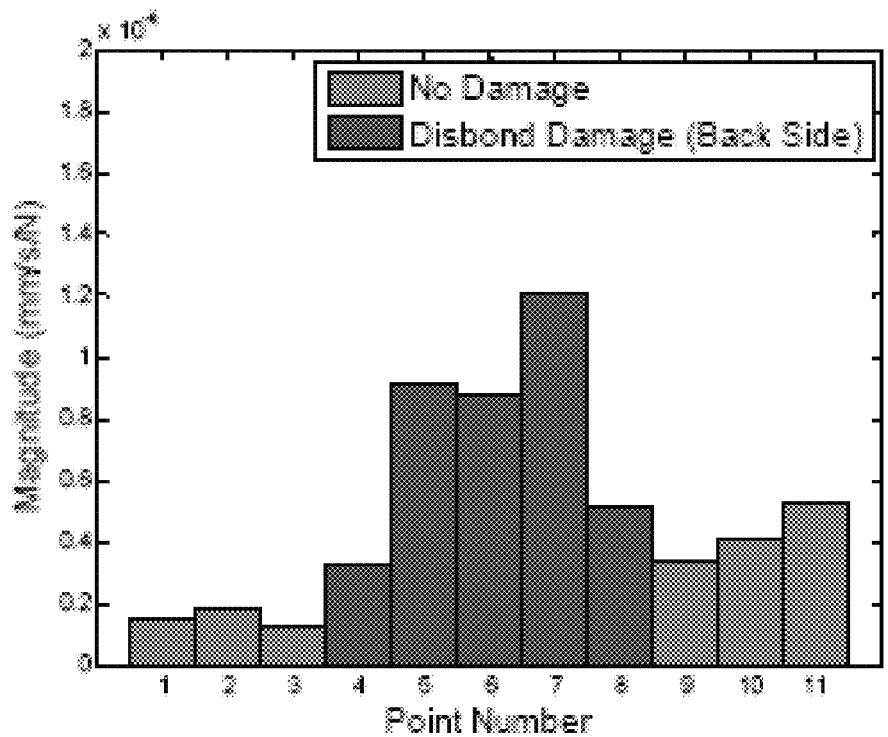

The influence of each measured direction (transverse, lateral, and longitudinal) varies for different damage mechanisms and locations. However, taking the product of the transverse, lateral, and longitudinal summation results also produces a damage index. FIGS. 9(a) and (b) show the final damage indices produced by taking the product of the three orthogonal directions for the core damage location and disbond damage on the back side of the panel, respectively.

As seen in FIG. 8(d) and FIGS. 9(a) and (b), each of the damage mechanisms investigated (shown in FIG. 2(c)) were accurately detected by comparing two frequency response functions collected using the two distinct amplitude excitations. This comparison was used to locate nonlinear response characteristics on the panel that were exhibited in the damaged region. Each of the damage locations appeared to display the largest nonlinear response towards the center of the damage region. The behavior of the points near the boundary of the damage may come about from coupling effects between the approximately linear response of the undamaged panel section and the nonlinear response of the damaged panel section. This trend is also consistent for the three damage mechanisms investigated in this paper.

Figure 10:
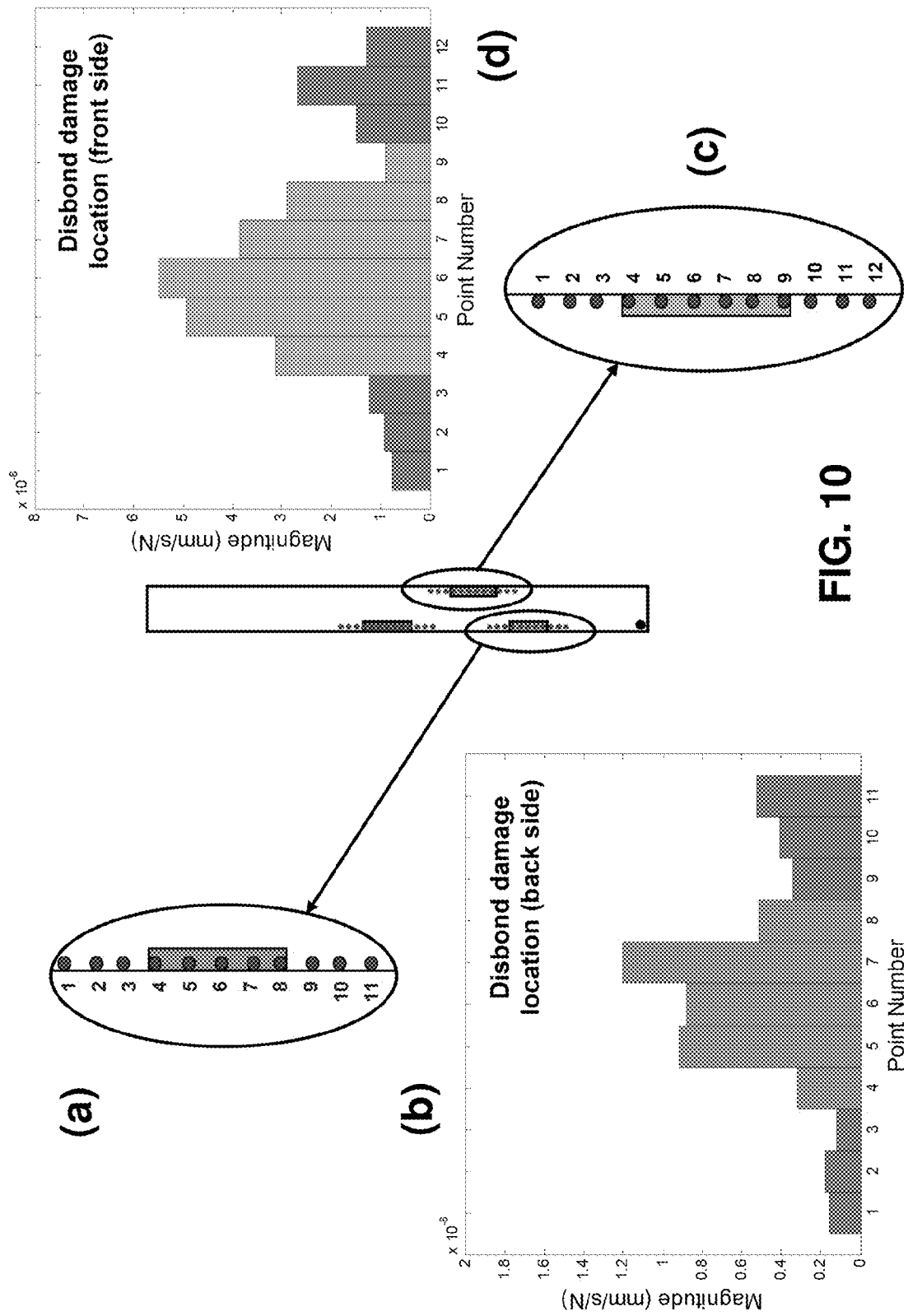
FIG. 10 show the (a) point numbers in the vicinity of the disbond (backside), (b) the damage indices at the various point numbers and (c) point numbers in the vicinity of the disbond (frontside) and (d) the damage indices at the various point numbers. (Refer to the numbering system in FIG. 7.)

FIGS. 10(b) and 10(d) show damage indices at various points for the disbond damage both back and front, respectively. FIGS. 10(a) and 10(c) graphically show the location of the point numbers relative to the areas of damage. It can be seen that the calculated magnitudes are effective in locating the damaged areas.

FIGS. 11(b), 11(c), and 11(d) show shaded contour plots of damage indices of a portion of the test panel in the region of the damaged core. FIG. 11(b) shows a damage index contour from 315 to 515 Hz, a frequency range of about six-tenths octave. FIG. 11(c) shows the damage indices contour in a frequency range from 515 to 710 Hz, a span of about four-tenths octave. FIG. 11(d) shows a contour plot of the damage indices in the same region of the panel over a frequency range from 715 to 915 Hz, a span of about three-tenths octave. It is to be appreciated that the location of damage can be more readily identified by reviewing damage indices in selected frequency bands. This is similar to the observation made with regards to FIGS. 6(b) and (c) relative to FIG. 6(a). In those cases, damage was more apparent in some frequency bands, as well as more generally in the longitudinal and lateral measurement directions.

In a second experimental validation of one embodiment of the present invention, a reference-free damage detection approach previously discussed was applied to a carbon fiber composite panel to investigate the damage detection capability for more realistic damage mechanisms. As previously discussed, damage mechanisms such as core cracking and disbonds were investigated on fiberglass composite specimens where the damage was introduced by placing cuts in the core or between the core and face sheets of the specimen investigated. In this validation, impact damage was applied to a carbon fiber composite panel in order to introduce damage which was more representative of what is seen in reality. The scanning laser vibrometer is used to measure the surface velocity of the panel to a sine sweep excitation and the resulting frequency response functions produced are analyzed to determine locations on the panel displaying the largest nonlinear response properties. Several different levels of damage are investigated at various locations on the panel, and thermal images of a similar panel are shown to confirm the damage indices produced through the measurement and analysis obtained with the scanning laser vibrometer. In addition, it is shown that investigation of nonlinearities at increasingly higher frequency ranges allows for better localization of the damage.

Impact damage on a carbon fiber sandwich panel was investigated experimentally using a three-dimensional scanning laser vibrometer as shown in FIG. 1(a). The forced frequency response of the panel to a sine sweep excitation was measured at specified points on the panel, and nonlinear response characteristics were identified. The areas on the panel displaying the largest nonlinear response characteristics were indicative of subsurface damage. Other aspects of the experimental setup are shown in FIG. 15.

The panel investigated consisted of carbon fiber face sheets sandwiching an Aramid honeycomb core. A diagram depicting the layout of the panel is shown in FIG. 15. This diagram shows the four carbon fiber plies on either side of the honeycomb core, as well as the orientations of the fibers in each ply. A description of the material used for each layer along with the ply angle and thickness is given in Table 1. The panel was cut to a length of 26 in and a width of 12 in.

TABLE 1

Description of each layer of the carbon fiber composite panel

| Layer Number | Description | Ply Angle (degrees) | Thickness (in) |
| --- | --- | --- | --- |
| 1 | 200 gsm 3K Carbon 2 × 2 Twill | 0 | 0.00866 |
| 2 | 300 gsm Std. Modulus Carbon Uni T700 | 0 | 0.01180 |
| 3 | 600 gsm Carbon/Epoxy Sprint | 45 | 0.02360 |
| 4 | 300 gsm Std. Modulus Carbon Uni T700 | 90 | 0.11800 |
| 5 | Aramid Honeycomb ⅛-3 lb | 0 | 0.50000 |
| 6 | 300 gsm Std. Modulus Carbon Uni T700 | 90 | 0.11800 |
| 7 | 600 gsm Carbon/Epoxy Sprint | 45 | 0.02360 |
| 8 | 300 gsm Std. Modulus Carbon Uni T700 | 0 | 0.01180 |
| 9 | 200 gsm 3K Carbon 2 × 2 Twill | 0 | 0.00866 |

Figure 15A:
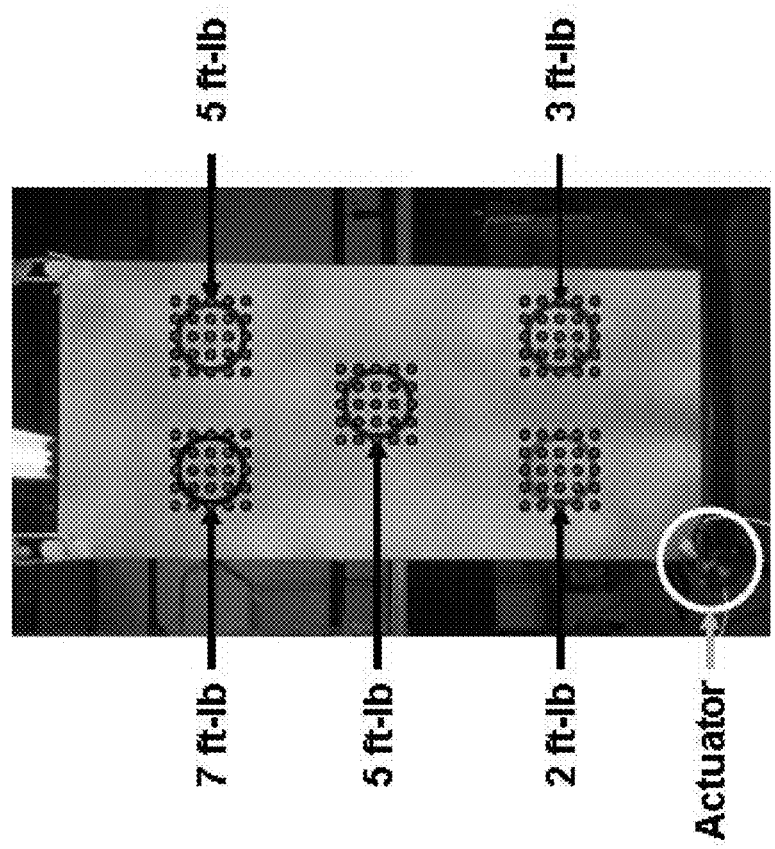

In order to introduce damage to the panel at controlled levels, an Instron Dynatup impact tower (model 9259HV) was used to impact the panel at five locations. Varying impact energies of 2, 3, 5, and 7 ft-lb were used. FIG. 15(a) shows the locations and energies of the impacts on the panel. The impact damage introduced face sheet cracking and core crushing at the point of impact, as well as delamination around the point of impact. The severity of the damage at the point of impact and the size of the delamination varied mainly based on the impact energy. Whereas in the previous example the damage mechanisms investigated were simulated disbonds or core cracking, here, the damage introduced by the impacts are different and the damage mechanisms are coupled together.

A PCB piezoelectric actuator (model 712A02) with a PCB impedance head (model 288D01) was attached at a skewed angle to the bottom left hand corner of the panel in order to excite the panel and measure the input force to the panel. The actuator location is highlighted in FIG. 15(*a*). A sine sweep excitation from 100 to 5000 Hz was used for the excitation signal with a sample time of 1.28 s. Various excitation amplitudes were used to excite the panel. FIG. 14 shows a representative time history of the forcing function at a particular frequency. A grid of measurement points was created about each damage location through the scanning laser vibrometer software. These grids are shown in FIG. 15(*a*). Each grid consisted of 25 points and was centered about the point of impact. In addition, each grid covered an area of approximately 4 square inches, giving about 1 inch spacing between grid points.

The scanning laser vibrometer measures the surface velocity of the panel at each grid point in three orthogonal directions. The frequency response function relating the input force to the panel with the output surface velocity in the transverse, lateral, and longitudinal directions is computed within the scanning laser vibrometer software. One sample was taken for each sine sweep excitation, and twenty-five averages were collected for each measurement point. Consecutive scans at different excitation amplitude levels were performed for each damage location.

The frequency response functions obtained from varying amplitude excitation levels were compared in order to identify locations displaying nonlinear response properties to the sine sweep excitation. As discussed earlier for fiberglass composite panels, the areas displaying the largest nonlinear response properties are indicative of subsurface damage. This same analysis approach was applied to the carbon fiber panel to investigate the behavior of the damage introduced by the impacts. The magnitudes of the frequency response functions obtained from a high and a low amplitude excitation were compared by computing the absolute value of the difference between the two frequency response functions. A summation of this difference across the frequency range from 315 to 850 Hz was computed for each measurement direction and a damage index was then created based on the product of the results in the transverse, lateral, and longitudinal directions. The measured points displaying larger nonlinear response properties were assigned higher damage index values. It is understood that other embodiments of the present invention contemplate other indices and algorithms for establishing a damage index. Another example of a damage indices contemplated by various embodiments of the present invention is the product of the velocity spectral power calculation among the transverse, lateral, and longitudinal measurement axes.

FIGS. 16(*a*) and (*b*) show the frequency response functions of several points on the surface of the object shown in FIG. 12 when exposed to low amplitude forcing excitation and high amplitude forcing excitation, respectively. The frequency response functions relate the output surface velocity measurement to the input force measured through the force sensor. FIG. 16(*c*) is a plot of the absolute value of the difference between the two frequency response functions shown in FIGS. 16(*a*) and (*b*). It can be seen that there are significant responses indicating differences in magnitude for all three points in the range from about 1100 Hz to about 1300 Hz. Thus, the nonlinearities in a response induced by material damage can be observed by comparisons of the difference between frequency response functions at two excitation amplitudes. The plots of FIGS. 16(*a*) and (*b*) are the frequency response functions for three points on the panel. These functions relate the output surface of velocity measurement (for the transverse direction measurement) to the input force measurement measured through the impedance head (i.e., force sensor). The frequency response estimates were prepared using an H1 estimator which assumes some noise on the output.

Further, it is observed that points within the damaged region exhibit larger changes than undamaged regions of the panel. FIG. 16(*c*) shows that up to about 1000 Hz the velocity response of the points is relatively linear with the change in excitation amplitude. However, in the region from about 1100 to about 1300 Hz these three points exhibit signification nonlinear behavior. Within this frequency band, a comparison of the absolute differences of frequency response functions show that the measurement points located on the damage display the largest nonlinear response compared to the points located away from the damage.

FIG. 17 illustrates the nonlinear responses in a pictorial manner. As shown in FIG. 17(*a*), a damage index is selected within the frequency range of 1000 to 1400 Hz. Data in this frequency range for the points indicated in FIG. 17(*b*) was then developed and interpolated to produce a damage index shading as shown. The area of panel damage is clearly evident in the center of the plot.

Unlike the fiberglass panels discussed previously, which were very highly damped, the carbon fiber panels investigated in this example were lightly damped. Because of the low damping, the higher excitation frequencies were not damped out, allowing a response to be obtained across a larger frequency range. In addition, care had to be taken to ensure the panel was not overexcited, particularly at locations close to the excitation source. Excitation amplitudes that were too high at locations close to the excitation source introduced nonlinearities that were not due to material damage, and can bring error into the damage index results. To determine the optimal excitation levels for this analysis, an amplitude study was performed at the 5 ft-lb impact location at the top of the panel. The damage indices produced for different combinations of input voltages to the actuator are shown in FIG. 18. The approximate location of the impact is highlighted in each damage index by the small black circle. Due to the coarse nature of the 25 point grids used in the measurement, interpolation was used between grid points to obtain a continuous damage index.

As seen from FIG. 18, the choice of high and low amplitude excitation levels had an effect on the damage index produced. However, it is noted that the areas in the damage indices indicating the highest damage levels are located in the vicinity of the impact damage (taking into account the coarse nature of the grids used), which is where delamination between the carbon fiber plies occurred. The results of the amplitude study suggested that the largest spread between high and low amplitude excitation levels was acceptable. However, further tests performed at the other impact locations closer to the excitation source limited the high amplitude excitation level, due to excessive excitation of the panel. The maximum excitation amplitude that was could be used at the 2 ft-lb and 3 ft-lb impact locations was a 10 V input to the actuator.

The ordinary coherence for the high and low amplitude frequency response functions was checked to verify that the surface velocity output was correlated with the input force for the measurements being performed. The coherence in the transverse direction was near unity across the excitation range except where antiresonances occurred in the frequency response functions, as expected. In the lateral and longitudinal directions, the coherence was less than unity across the excitation range due to the small responses measured in those in-plane directions. However, the coherence increased at peaks in the frequency response functions suggesting good correlation at frequencies where a measurable response was produced.

Damage indices were produced for each of the impact locations using the measurement grids shown in FIG. 15(a). The results were overlaid on the damage locations and are shown in FIG. 19. The high and low amplitude excitation levels used were 10 V and 5 V, respectively. These amplitudes were chosen in order to be consistent with the results for other damage locations. It is noted that the damage indices were created individually for each impact location, and do not reflect the severity of damage relative to each other.

As seen in FIG. 19, the damage index results in each case indicate that the point located directly on the impact location (the point at the center of each damage index) does not display large nonlinear response properties when a change in excitation amplitude is experienced. This is most likely due to the cracking and change of shape of the top face sheet at the impact location. For the three impact locations on the upper half of the panel, including the two 5 ft-lb impacts and the 7 ft-lb impact, the delamination surrounding the point of impact is apparent in the computed damage indices. The interpolation used in the creation of the damage indices resulted in a less than desirable image of the damage shape and size. However, the result showed that sub-surface damage is present in the impacted region of the panel. If more information about the overall shape and size of the damage was desired, a finer grid could be created to obtain those results.

The damage indices created for the 2 and 3 ft-lb impacts located on the bottom half of the panel do not clearly indicate damage from the impacts. This is most likely a result of the low damage levels compared to the 5 and 7 ft-lb impacts, the close proximity of the damage to the actuator location, or a combination of both of these reasons. As described previously, the close proximity of these damage locations to the excitation source may have caused nonlinearities introduced by material damage to be washed out by nonlinearities introduced through the response of the panel to a large excitation. Measurement points experiencing large deflections may falsely indicate damage through the analysis method performed. In order to more accurately identify the damage introduced by the impact damage to this section of the panel, it is helpful to reduce the amplitude of the excitation so that fewer nonlinearities are introduced by the actuator overexciting the panel. The actuator can be moved to another location on the panel, such as the upper right corner of the panel. This second actuator location, if coupled with the results from the current actuator location, would allow for more accurate identification of the damage introduced by all of the impact locations investigated.

In order to justify the results obtained and shown in FIG. 19, thermal images were produced for a second carbon fiber panel, cut to the same dimensions as the panel used in the scanning laser vibrometer investigations, with the same impact locations and energies as is depicted in FIG. 15(a). An infrared camera was used to obtain the thermal images, providing visual images of the shape and scope of the subsurface damage in the panel. The images obtained for each of the damage locations are shown in FIG. 20(a). In addition, FIG. 20(b) shows a clearer image of the delamination around the 7 ft-lb impact on this second panel.

It is clear from FIG. 20(a), that both 5 ft-lb impacts and the 7 ft-lb impact produced visible subsurface damage in the region surrounding the impact location. However, very little, if any, subsurface damage is seen at either the 2 ft-lb or the 3 ft-lb impact locations. This is most likely a reason why the scanning laser vibrometer analysis produced poor results at these two damage locations. A seam in the panel running down the right side of the panel can also be seen in the images produced for both 5 ft-lb impacts as well as the 3 ft-lb impact. This is a manufacturing defect which could also affect the results obtained through measurement with the scanning laser vibrometer. FIG. 20(b) shows the delamination resulting from the 7 ft-lb impact. The blue region in the immediate area of the impact suggests subsurface damage near the surface, while a yellow region can be seen extending above and below this blue region. This shows a deeper delamination extending even further from the point of impact. The peanut shaped behavior of these delaminations comes about from the stacking sequence of the carbon fiber plies.

Similar research on composite specimens has shown that higher modal frequencies may be used to detect and locate damage. This was investigated on the first carbon fiber panel with the scanning laser vibrometer for the 5 ft-lb impact in the upper corner of the panel. The original range used to create a damage index for this impact location was from 315-850 Hz (a range of less than about two octaves). In order to see the effects of higher frequency ranges, additional damage indices were created using the summation of the difference between high and low amplitude excitation levels for frequency ranges of 850-1500 Hz (a range of less than about one octave) and 1500-2500 Hz (a range of less than about one octave). The damage indices for these three frequency ranges are shown in FIG. 21. This analysis shows that the damage becomes more localized at higher frequencies. In addition, the error in the measurement seems to decrease as the frequency range is increased. As seen in FIG. 21, the frequency range from 1500-2500 Hz gives the clearest indication of damage about the point of impact, whereas the frequency range from 315-850 Hz provides a less clear image of the damage location.

The panel setup shown in FIG. 12(b), representing a fixed boundary condition was analyzed in the same method previously described. This panel is pictured again in FIG. 22(a) and (b), where FIG. 22(a) shows the front side of the panel and two measurement areas used in the analysis while FIG. 22(b) shows the back side of the panel. This carbon fiber sandwich panel impact damage was applied at two locations. The lower left square in FIG. 22(a) highlights the area about impact damage of magnitude 25 ft-lb applied to the front side of the panel using a 2 inch diameter tup in the impact tower. The upper right square in FIG. 22(a) highlights the area about impact damage of magnitude 30 ft-lb applied to the back side of the panel. Damage index results were produced by identifying the regions of the panel displaying the largest nonlinear response properties. These results are depicted in FIG. 22(c), (d), and (e) for the cases described in FIG. 22. For example, FIG. 22(c) depicts the result produced for a square grid consisting of 9 points located about the damage introduced to the front side of the panel where the center point was the point located on the damage. Each of these damage index plots correctly identified the respective damage locations on the panel using the method described above.

In some embodiments, the measurements that are taken may be limited based on the construction of the panel, the mounting of the panel, and the expected damage mechanism. For example, with a panel mounted within a frame, it is possible to use only one measurement direction, such as the transverse direction measurement of velocity. In yet other panels, two or three measurement directions may be used in the calculation of the damage indices. In some embodiments, the datasets are taken along specific measurement axes based on the damage mechanisms believed to be detected. For example, on a mounted panel receiving impact damage, the transverse direction of measurement may be sufficient by itself. It has been found that the transverse measurement direction is more sensitive to core damage (such as that created by the impact). In contrast, the in-plane measurement directions are more sensitive to face sheet damage, such as disbond and delamination.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for determining the structural integrity of a panel, comprising:
   providing a non-contact measurement system and an excitation source configured to provide a vibratory load;
   exciting the panel with the source at at least one frequency at a first amplitude;
   acquiring first velocity data with the system of at least one point on the surface of the panel during said exciting at a first amplitude;
   exciting the panel with the source at at least the one frequency at a second amplitude different than the first amplitude;
   acquiring second velocity data with the system for the point on the surface of the panel during said exciting at a second amplitude;
   correcting at least one of the first data with a factor corresponding to the first amplitude or the second data with a factor corresponding to the second amplitude;
   comparing the first data to the second data after said correcting;
   identifying non-linear behavior of the point from said comparing; and
   determining the structural integrity of the panel from said comparing.

2. The method of claim 1 wherein said identifying includes analyzing the first data and the second data using a coherence function.

3. The method of claim 1 wherein said vibrating is random vibration and identifying includes analyzing the first data and the second data using a bispectra technique.

4. The method of claim 1 wherein said vibrating is sinusoidally swept vibration and identifying includes analyzing the first data and the second data by the method of restoring forces.

5. The method of claim 1 wherein said identifying includes analyzing the first data and the second data using autoregressive exogenous input frequency models.

6. The method of claim 1 wherein said identifying includes analyzing the first data and the second data using transmissibility functions.

7. The method of claim 1 wherein said identifying includes analyzing the first data and the second data by nonlinear identification through feedback of the outputs.

8. The method of claim 1 wherein said identifying includes analyzing the first data and the second data by vibro-acoustic modulation.

9. The method of claim 1 wherein said correcting the first data is by normalizing the velocity magnitudes by the first amplitude.

10. The method of claim 1 which further comprises creating a damage index for the point during said comparing and said determining is based on the damage indices.

11. The method of claim 1 wherein said exciting at a second amplitude is at a plurality of frequencies within a predetermined range of frequencies.

12. The method of claim 11 wherein said exciting at a first amplitude is at a plurality of frequencies within a predetermined range of frequencies.

13. The method of claim 12 wherein said comparing is within a predetermined band of frequencies that is substantially narrower than the predetermined range.

14. The method of claim 1 which further comprises providing a panel that is a fabricated as a laminated composite.

15. The method of claim 1 which further comprises providing a panel that includes a honeycomb core.

16. The method of claim 1 wherein the system is a laser measurement system and said acquiring at a first amplitude is with the laser system.

17. The method of claim 1 wherein said vibrating is with a piezoelectric actuator attached to the panel.

18. The method of claim 1 wherein the panel has a surface and said first vibrating is mechanically vibrating the panel in a direction that is not normal to the surface.

19. A method for determining the structural integrity of a panel, comprising:
   establishing a three axis coordinate system on the panel;
   establishing a plurality of discrete points on the panel;
   vibrating the panel simultaneously in each axis of the coordinate system at a first amplitude;
   measuring the three axis velocity at each of the points during said vibrating at a first amplitude;
   vibrating the panel simultaneously in each axis of the coordinate system at a second amplitude different than the first amplitude;
   measuring the three axis velocity at each of the points during said vibrating at a second amplitude;
   comparing the measured velocity during said vibrating at the first amplitude to the measured velocity during said vibrating at the second amplitude; and
   determining the structural integrity of the panel from said comparing.

20. The method of claim 19 wherein said determining is by identifying a response of a point on the panel to said second vibrating that is non-linear with respect to the response of the point to said first vibrating.

21. The method of claim 19 wherein said comparing includes non-linear analysis.

22. The method of claim 21 wherein said comparing includes analyzing the first measured velocities and the second measured velocities using a coherence function.

23. The method of claim 21 wherein said vibrating is random vibration and comparing includes analyzing the first measured velocities and the second measured velocities using a bispectra technique.

24. The method of claim 21 wherein said vibrating is sinusoidally swept vibration and comparing includes analyzing the first measured velocities and the second measured velocities by the method of restoring forces.

25. The method of claim 21 wherein said comparing includes analyzing the first measured velocities and the second measured velocities using autoregressive exogenous input frequency models.

26. The method of claim 21 wherein said comparing includes analyzing the first measured velocities and the second measured velocities using transmissibility functions.

27. The method of claim 21 wherein said comparing includes analyzing the first measured velocities and the second measured velocities by nonlinear identification through feedback of the outputs.

28. The method of claim 21 wherein said comparing includes analyzing the first measured velocities and the second measured velocities by vibro-acoustic modulation.

29. The method of claim 19 which further comprises creating a damage index for each of the points during said comparing and said determining is based on the damage indices.

30. The method of claim 29 wherein the damage index for each point corresponds to the difference in velocity of the point between said first vibrating and said second vibrating.

31. The method of claim 29 wherein the first velocity data is normalized by the first amplitude and the second velocity data is normalized by the second amplitude, and the damage index for each point corresponds to the difference in normalized velocity of the point between said first vibrating and said second vibrating.

32. The method of claim 19 which further comprises providing a panel that is a structural member and remains at least partly integrated into a larger assembly and said first vibrating is of the integrated panel.

33. The method of claim 19 which further comprises providing a separated panel that was integrated as a structural member.

34. The method of claim 19 wherein the panel has a surface and said first vibrating is mechanically vibrating the panel in a direction that is not normal to the surface.

35. The method of claim 19 wherein said establishing of discrete points is on a surface of the panel, and each said measuring is with a non-contact measurement system.

\* \* \* \* \*